US007993931B1

(12) United States Patent
Chen

(10) Patent No.: US 7,993,931 B1
(45) Date of Patent: Aug. 9, 2011

(54) OXYGEN-18 LABELED ORGANIC ACIDS AND USE IN DIAGNOSING METABOLIC DISORDERS

(75) Inventor: Su Chen, Aliso Viejo, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 2275 days.

(21) Appl. No.: 10/696,051

(22) Filed: Oct. 28, 2003

(51) Int. Cl.
*G01N 33/00* (2006.01)
(52) U.S. Cl. .................. 436/129; 436/127; 436/173
(58) Field of Classification Search .................. 436/127, 436/128, 129, 130, 131, 132, 133, 56, 173, 436/178, 811; 210/656
See application file for complete search history.

(56) References Cited

U.S. PATENT DOCUMENTS

| 5,686,311 A * | 11/1997 | Shaw | 436/86 |
| 2002/0019056 A1 * | 2/2002 | Shushan et al. | 436/129 |
| 2005/0070023 A1 * | 3/2005 | Nguyen et al. | 436/129 |

OTHER PUBLICATIONS

Leis et al. "Synthesis of [18O2]valproic acid and its use as an internal standard for the quantitative measurement by gas chromatography-electron ionization mass spectrometry". 2003. J. Chrom. B. vol. 784, pp. 69-75.*
Peterson et al. "Synthesis of regiospecifically labeled [18O]glycolic acid and [18O]acyldihydroxyacetone phosphate". 1988. Journal of Lipid Research. vol. 29, pp. 94-101.*
Pang, CCP. "Laboratory investigations of inherited metabolic diseases." 1996. Hong Kong Medical Journal. vol. 2, No. 3, pp. 264-273.*
Chen and Carvey, "Validation of Liquid-Liquid Extraction Followed by Flow-Injection Negative Ion Electrospray Mass Spectrometry Assay to Topiramate in Human Plasma," *Rapid Commun Mass Spectrom*, 15:159-163 (2001).
Clay and Murphy, "New Procedure for Isolation of Amino Acids Based on Selective Hydrolysis of Trimethylsilyl Derivatives," *Journal of Chromatography*, 164: 417-426 (1979).
Gleispach, et al., "Neuroblastoma Screening: Labeling of HVA and VMA for Stable Isotope Dilution Gas Chromatography-Mass Spectrometry," Supplement to *Nutrition*, 11: 604-606 (1995).
Heales and Leonard, "Diagnosis of Medium Chain Acyl CoA Dehydrogenase Deficiency by Measurement of *cis*-4-Decenoic Acid in Dried Blood Spots," *Clinica Chimica Acta*, 209: 61-66 (1992).
Ikegawa et al., "Separation and Detection of Bile Acid 24-Glucuronides in Human Urine by Liquid Chromatography Combined With Electrospray Ionization Mass Spectrometry." *Analytical Sciences*, 15: 625-631 (1999).
Jakobs and de Grauw, "A Fatal Case of 2-Keto-, 2-Hydroxy- and 2-Aminoadipic Aciduria: Relation of Organic Aciduria to Phenotype?" *Inher. Metab. Dis.* 15: 279-280 (1992).
Jorg Leis et al., "Synthesis of [$^{18}O_2$] Valproic Acid and Its Use as an Internal Standard For the Quantitative Measurement by Gas Chromatography-Electron Ionization Mass Spectrometry," *Journal of Chromatography B*, 784: 69-75 (2003).

(Continued)

*Primary Examiner* — Yelena G Gakh
*Assistant Examiner* — David Weisz
(74) *Attorney, Agent, or Firm* — Foley & Lardner LLP

(57) ABSTRACT

Provided are methods and compositions for quantitatively measuring the amount of an unlabeled organic acid in a sample. Oxygen-18 labeled organic acids are used as internal standards to adjust for the loss of a structurally similar or identical unlabeled organic acid through processing required for its detection, such as by mass spectrometry. The methods of the invention are useful for diagnosing inborn errors of metabolism in an individual by quantitating signature organic acids in body fluids such as urine or plasma.

43 Claims, 26 Drawing Sheets

OTHER PUBLICATIONS

Kushnir et al., "Analysis of Dicarboxylic Acids by Tandem Mass Spectrometry. High-Throughout Quantitative Measurement of Methylmalonic Acid in Serum, Plasma and Urine." *Clin Chem* 47(11): 1993-2002 (2001).

Liebich and Först, "Hydroxycarboxylic and Oxocarboxylic Acids in Urine: Products From Branched-Chain Amino Acid Degradation and From Ketogenesis," *Journal of Chromatography*, 309: 225-242 (1984).

Magera et al., "Determination of Homovanillic Acid in Urine by Stable Isotope Dilution and Electrospray Tandem Mass Spectrometry," *Clinica Chimica Acta*, 306: 35-41 (2001).

Mirgorodskaya et al., "Quantitation of Peptides and Proteins by Matrix-Assisted Laser Desorption/Ionization Mass Spectrometry Using $^{18}$O-Labeled Internal Standards," *Rapid Commun. Mass. Spectrom.*, 14: 1226-1232 (2000).

Murphy and Clay, "Synthesis and Back Exchange of $^{18}$O Labeled Amino Acids For Use as Internal Standards With Mass Spectrometry." *Biomedical Mass Spectrometry*, vol. 6, No. 7: 309-314 (1979).

Pitt et al., "Comprehensive Screening of Urine Samples for Inborn Errors of Metabolism by Electrospray Tandem Mass Spectrometry," *Clin Chem* 48(11): 1970-1980 (2002).

Shigematsu et al., "A Simple Method of Determining 4-Hydroxyisovaleric Acid and Its Level in a Patient with Isovaleric Acidemia," *Clinica Chimica Acta*, 138: 333-336 (1984).

Sweetman, "Organic Acid Analysis," *In* (Hommes, Ed.) *Techniques in diagnostic human biochemical genetics* Wiley-Liss: New York, 143-176 (1991).

Truscott et al., "The Identification of 3-Keto-2-Methylvaleric Acid and 3-Hydroxy-2-Methylvaleric Acid in a Patient With Propionic Acidemia," *Biomedical Mass Spectrometry*, 6: 294-300 (1979).

Tserng et al., "Urinary 3-Hydroxyadipic Acid 3,6-Lactone: Structural Identification and Effect of Fasting in Adults and Children," *Metabolism*, 38: 655-661 (1989).

Van Rooyen et al., "Identification of the Steroisomeric Configurations of Methylcitric Acid Produced by *si*-Citrate Synthase and Methylcitrate Synthase Using Capillary Gas Chromatograpy-Mass Spectrometry," *J. Inher. Metab. Dis.*, 17: 738-747 (1994).

Veldink et al., "Oxygen Transfer in the Enzymatic Conversion of $^{18}$O-Labelled Linoleic Acid Hydroperoxide into the 12-Keto-13-Hydroxy-Octadec-*CIS*-9-Enoic Acid," *FEBS Letters*, 7: 188-190 (1970).

Youhnovski, et al., "Determination of Hydroxyoctadecadienoic Acids," *Z. Naturforsch*, 58c: 268-279 (2003).

Zytkovicz et al., "Tandem Mass Spectrometric Analysis for Amino, Organic, and Fatty Acid Disorders in Newborn Dried Blood Spots: A Two-Year Summary From the New England Newborn Screening Program." *Clin Chem* 47(11): 1945-1955 (2001).

\* cited by examiner

Figure 11. Quantitative Analyses of 2-Oxo Glutaric Acid Using $^{18}$O-Standard

| nMol/mL | Sta. Area | I.S Area | Ratio |
|---|---|---|---|
| 10 | 99282 | 1911058 | 0.051951 |
| 20 | 159741 | 1548286 | 0.103173 |
| 100 | 812365 | 1574774 | 0.515861 |
| 200 | 1682033 | 1731756 | 0.971288 |
| 600 | 6660242 | 2457755 | 2.709888 |

| a | b |
|---|---|
| 0.0045 | 0.0366 |
| 0.0045 | 0.0366 |
| 0.0045 | 0.0366 |
| 0.0045 | 0.0366 |

|  | Sam. Area | I.S. Area | x=(y-b)/a (nMol/mL) |
|---|---|---|---|
| QC sample-1 (25 nM) | 204106 | 1522543 | 21.65689 |
| QC sample-2 (500 nM) | 4760764 | 2038057 | 510.9628 |
| Spiked sample-1 (50 nM) | 436352 | 1686953 | 49.34729 |
| Spiked sample-2 (200 nM) | 1802739 | 1848618 | 208.5738 |

Figure 13. Quantitative Analyses of 2-OH-Butyric Acid Using $^{18}$O Standard

| nMol/mL | Sta. Area | IS. Area | Ratio |
|---|---|---|---|
| 10 | 262735 | 6538901 | 0.04018 |
| 20 | 252854 | 4361156 | 0.057979 |
| 100 | 1350819 | 5846408 | 0.231051 |
| 200 | 2752413 | 6474802 | 0.425096 |
| 600 | 7127199 | 5745837 | 1.240411 |

Standard Curve of 2-OH-Butyric Acid (A mixture was spiked into Urine)

y = 0.002x + 0.0208
R² = 0.9999

| a | b |
|---|---|
| 0.002 | 0.0208 |
| 0.002 | 0.0208 |
| 0.002 | 0.0208 |
| 0.002 | 0.0208 |
| 0.002 | 0.0208 |

|  | Sam. Area | I.S. Area | x=(y-b)/a (nMol/mL) |
|---|---|---|---|
| QC sample-1 (25 nM) | 455896 | 5948434 | 27.92067 |
| QC sample-2 (150 nM) | 2193354 | 6626783 | 155.0916 |
| QC sample-3 (500 nM) | 5566084 | 5866775 | 463.9734 |
| Spiked sample-1 (50 nM) | 644325 | 5143162 | 52.239 |
| Spiked sample-2 (400 nM) | 5762361 | 6306218 | 446.4793 |

Figure 15. Quantitative Analyses of 3-OH-3-Methyl Butyric Acid Using $^{18}$O-Standard

| nMol/mL | Sta. Int. | IS Int. | Ratio |
|---|---|---|---|
| 10 | 4446 | 121509 | 0.03659 |
| 20 | 4436 | 92023 | 0.048205 |
| 100 | 14663 | 91820 | 0.159693 |
| 200 | 28954 | 103378 | 0.280079 |
| 600 | 74919 | 92577 | 0.809261 |

Standard Curve of 3-OH-2-methylButyric Acid (A mixture was spiked into Urine)

$y = 0.0013x + 0.0234$
$R^2 = 0.9999$

| a | b |
|---|---|
| 0.0013 | 0.0234 |
| 0.0013 | 0.0234 |
| 0.0013 | 0.0234 |
| 0.0013 | 0.0234 |
| 0.0013 | 0.0234 |

|  | Sam. Int. | I.S. Int. | x=(y-b)/a (nMol/mL) |
|---|---|---|---|
| QC sample-1 (25 nM) | 4897 | 79261 | 29.52556 |
| QC sample-2 (150 nM) | 23435 | 104988 | 153.7046 |
| QC sample-3 (500 nM) | 61873 | 99796 | 458.9191 |
| Spiked sample-1 (50 nM) | 9229 | 101920 | 51.65493 |
| Spiked sample-2 (400 nM) | 64894 | 109735 | 436.9001 |

Figure 17. Quantitative Analyses of 2-OH-Isocaproic and 5-OH-Hexanoic Acids Using $^{18}$O-Standard Figure 19. Quantitative Analyses of 4-OH-Phenyl Acetic Acid Using $^{18}$O-Standard

| nMol/mL | Sta. Area | IS Area | Ratio |
|---|---|---|---|
| 10 | 3014243 | 57760161 | 0.052186 |
| 20 | 2798947 | 43929289 | 0.063715 |
| 100 | 8364944 | 44761329 | 0.186879 |
| 200 | 14302292 | 44602241 | 0.320663 |
| 600 | 36919659 | 43414038 | 0.850408 |

| a | b |
|---|---|
| 0.0014 | 0.0436 |
| 0.0014 | 0.0436 |
| 0.0014 | 0.0436 |
| 0.0014 | 0.0436 |
| 0.0014 | 0.0436 |

| | Sam. Area | I.S. Area | x=(y-b)/a (nMol/mL) |
|---|---|---|---|
| QC sample-1 (25 nM) | 3364167 | 45014908 | 22.23893 |
| QC sample-2 (150 nM) | 12175131 | 50417025 | 141.3489 |
| QC sample-2 (500 nM) | 28601769 | 45860639 | 414.3336 |
| Spiked sample-1 (50 nM) | 5087964 | 45749018 | 48.29623 |
| Spiked sample-2 (400 nM) | 31012101 | 45301685 | 457.8346 |

Figure 21. Quantitative Analyses of Glyceric Acid Using $^{18}$O-Standard

| nMol/mL | Sta. Area | IS Area | Ratio |
|---|---|---|---|
| 10 | 26501 | 801493 | 0.033065 |
| 20 | 31674 | 633191 | 0.050023 |
| 100 | 136532 | 647351 | 0.210909 |
| 200 | 256128 | 680422 | 0.376425 |
| 600 | 791264 | 694796 | 1.138844 |

| | a | b |
|---|---|---|
| | 0.0019 | 0.0138 |
| | 0.0019 | 0.0138 |
| | 0.0019 | 0.0138 |
| | 0.0019 | 0.0138 |
| | 0.0019 | 0.0138 |

| | Sam. Area | I.S. Area | x=(y-b)/a (nMol/mL) |
|---|---|---|---|
| QC sample-1 (25 nM) | 44323 | 608095 | 31.0991 |
| QC sample-2 (150 nM) | 228735 | 754818 | 152.2281 |
| QC sample-2 (500 nM) | 657868 | 722247 | 472.1384 |
| Spiked sample-1 (50 nM) | 74115 | 669773 | 50.97731 |
| Spiked sample-2 (400 nM) | 602067 | 728922 | 427.4574 |

Figure 23. Quantitative Analyses of Glutaric Acid Using $^{18}$O-Standard

| nM/mL | Sample | I.S | Ratio |
|---:|---:|---:|---:|
| 10 | 706042 | 14233824 | 0.049603 |
| 20 | 957477 | 10597092 | 0.090353 |
| 100 | 4807958 | 10465071 | 0.459429 |
| 200 | 9209660 | 11121729 | 0.828078 |
| 600 | 26198122 | 10991941 | 2.383394 |

Standard Curve of Glutaric Acid
(A mixture was spiked into urine)

y = 0.0039x + 0.0299
$R^2$ = 0.9994

| a | b |
|---:|---:|
| 0.0039 | 0.0299 |
| 0.0039 | 0.0299 |
| 0.0039 | 0.0299 |
| 0.0039 | 0.0299 |
| 0.0039 | 0.0299 |

|  | Sam. Area | I.S. Area | x=(y-b)/a (nMol/mL) |
|---|---:|---:|---:|
| QC sample-1 (25 nM) | 1342471 | 10520794 | 25.05171 |
| QC sample-2 (150 nM) | 7866679 | 12205842 | 157.59 |
| QC sample-3 (500 nM) | 21304159 | 9350480 | 576.5392 |
| Spiked sample-1 (50 nM) | 2518098 | 11005441 | 51.00124 |
| Spiked sample-2 (400 nM) | 16914895 | 9112873 | 468.2702 |

Figur 24

Figure 25. Quantitative Analyses of Butyryl, Tiglyl and Hexanoyl Glycines Using $^{18}$O Standard

OXYGEN-18 LABELED ORGANIC ACIDS AND USE IN DIAGNOSING METABOLIC DISORDERS

FIELD OF THE INVENTION

The present invention relates to oxygen-18 labeled organic acids and their utility in organic acid quantitation. More particularly, the invention relates to oxygen-18 labeled organic acids and their utility as internal standards in quantitatively analyzing organic acids from biological samples.

BACKGROUND OF THE INVENTION

The following description of the background of the invention is provided simply as an aid in understanding the invention and is not admitted to describe or constitute prior art to the invention.

Individuals with inborn errors of metabolism (IEM) can, in many cases, be identified by the presence of abnormal metabolites which are either non-existent or present in only very small amounts as compared to the urine of normal individuals. Such markers of metabolism include organic acids, which constitute a large variety of individual compounds. For example, inborn errors of metabolism associated with increased excretion of various acyl glycines, including isovaleryl, crotonyl, 3-methylcrotonyl, butyrol, 2-methylbutyryl and suberoyl glycines is known. Analyses of these glycines in human plasma and urine is used for the diagnosis of diseases such as medium chain acyl-CoA dehydrogenase deficiency, an error in mitochondrial β-oxidation of straight chain fatty acid, carboxylase deficiency, and 2-methylacetoacetyl CoA thiolase deficiency, as well as isovaleric acidaemia, propionic acidaemia and isovaleric acidaemia. See e.g., Zytkovicz et al., *Clin Chem* 47(11): 1945-1955 (2001).

Quantitative analyses of organic acids in urine or serum are usually performed by the procedures of extracting the acids from biological samples, chemical derivatization of extracted acids, and finally separation and detection of derivatized acids by gas chromatography-mass spectrometry (GC-MS) or in some cases by tandem mass spectrometry (MS/MS). See e.g., Sweetman, In (Homes, Ed.) "Techniques in diagnostic human biochemical genetics" Wiley-Liss, New York, page 143-174 (1991); Kushnir et al., *Clin Chem* 47(11): 1993-2002 (2002). Internal standards are used in some cases to predict the loss of an organic acid from processing so that the starting amount of the acid in the sample may be accurately calculated. However, there remains a continuing need for a wide range labeled organic acid internal standards to enable more accurate methodologies with greater ease of use in providing high throughput and lower overall cost detection of signature IEM.

SUMMARY OF THE INVENTION

Quantitative measurement of the amount of particular organic acids in a sample is important to accurately diagnose the existence of metabolic disorders in an individual. The present invention provides a method for quantitatively measuring organic acids in samples suspected of containing one or more organic acids. Thus, the present methods are designed to accurately measure the amount of an organic acid by adjusting for loss of the organic acid through processing required for its detection. The invention methods accomplish this by adding one or more oxygen-18 radiolabeled organic acids as internal standards to the sample to measure the recovery of organic acids following processing. The added oxygen-18 organic acid(s) can be identical to the organic acids to be determined or may be structurally similar. The oxygen-18 labeled organic acid(s) used to estimate recovery is preferably identical to the organic acid sought to be analyzed.

By "structurally similar," is meant that the organic acids all share significant structural characteristics such as key functional groups. For example, structurally similar organic acids of the group known as hydroxyl mono-acids include such acids having a single carboxyl acid group and a single hydroxyl group. Exemplary structurally similar hydroxyl mono-acids are well known in the art and include, for example, glycolic acid, lactic acid, 3-hydroxypropionic acid, 2-hydroxybutyric acid, 3-hydroxyisobutyric acid, 3-hydroxybutyric acid, 4-hydroxybutyric acid, 2-hydroxyisovaleric acid, 3-hydroxy-2-methylbutyric acid, 3-hydroxy isovaleric acid, 3-hydroxy-2-ethyl propionic acid, 3-hydroxyvaleric acid, 4-hydroxyisovaleric acid, 5-hydroxyhexanoic acid, 2-hydroxyisocaproic acid, 2-hydroxy-3-methyl valeric acid, 5-hydroxyhexanoic acid, 3-hydroxy-2-methyl valeric acid, 2-hydroxyphenyl acetic acid, 4-hydroxy phenyl acetic acid, 4-hydroxycyclohexyl acetic acid, phenyl-lacetic acid, 4-hydroxyphenyl propionic acid, 5-hydroxyindoleacetic acid, homovanillic acid, indoleacetic acid or 3-hydroxydodecanoic acid. Other groups of organic acids which each contain a variety of different yet structurally similar compounds include, for example, dihydroxy mono-acids, dicarboxyl organic acids, hydroxyl dicarboxyl acids, tricarboxyl acids, glycine conjugates and Oxo-acids (Keto acids).

In accordance with one aspect of the present invention, the amount of an organic acid in a sample is measured by a) adding to a sample suspected of containing the unlabeled organic acid to be measured, an amount of an oxygen-18 labeled organic acid structurally similar or identical to the unlabeled organic acid to be measured; b) processing the sample; c) measuring the amount of unlabeled organic acid and oxygen-18 organic acid in the processed sample; and d) using the amount of oxygen-18 organic acid measured in step c) to adjust the amount of unlabeled organic acid measured in the processed sample so as to reflect the amount of unlabeled organic acid originally present in the sample. In a preferred embodiment, if only a single oxygen-18 organic acid is used, the oxygen-18 labeled organic acid is not oxygen-18 labeled homovanillic acid.

In accordance with another aspect of the present invention, the amount of an organic acid sample is measured by a) adding to a sample suspected of containing the at least one unlabeled organic acid to be measured an amount of at least one oxygen-18 labeled organic acid selected from each of hydroxy mono-acid, dihydroxy mono-acid, dicarboxyl organic acid, hydroxyl dicarboxyl acid, tricarboxyl acid, glycine conjugate and oxo acid; b) processing the sample; c) measuring the amount of unlabeled organic acids and oxygen-18 organic acids in the processed sample; and d) using the amount of an oxygen-18 organic acid measured in step c) to adjust the amount of a structurally similar or identical unlabeled organic acid measured in the processed sample so as to reflect the amount of unlabeled organic acid originally present in the sample.

By "sample" is meant a sample obtained from a biological source, e.g., an organism, cell culture, tissue sample, and the like. A biological sample can, by way of non-limiting example, consist of or comprise blood, sera, plasma, urine, feces, epidermal sample, skin sample, cheek swab, sperm, amniotic fluid, cultured cells, bone marrow sample and/or chorionic villi. A body fluid sample is a preferred biological sample from which to measure organic acids using the invention methods. The term "sample" includes samples which have been processed to isolate or purify the organic acid.

In the case where the particular identify of the organic acid that is suspected of being present in the sample is not known before testing, more than one oxygen-18 labeled organic acid may be added to the sample. By increasing the number of different oxygen-18 labeled organic acids added to the sample, the likelihood is greater that the particular unlabeled organic acid present in the sample will be structurally similar or identical to one of the oxygen-18 labeled organic acids added to the sample as an internal standard.

In one embodiment, an oxygen-18 labeled organic acid(s) added to the sample is selected from the group consisting of hydroxyl mono-acid, dihydroxy mono-acid, dicarboxyl organic acid, hydroxyl dicarboxyl acid, tricarboxyl acid, glycine conjugate and oxo acid. In some embodiments, the sample to be tested will be spiked with at least one oxygen-18 organic acid from each of hydroxy mono-acid, dihydroxy mono-acid, dicarboxyl organic acid, hydroxyl dicarboxyl acid, tricarboxyl acid, glycine conjugate and oxo acid. Such sample would thus contain six different oxygen-18 labeled organic acids. In other embodiments, at least two oxygen-18 organic acids from each of the six groups would be added to the sample. In further embodiments, the number of labeled acids from each group may be 3, 4, 5, 6 and even all from each group disclosed herein (see Tables 1-7). It is desirable to have at least one internal standard present for each class of organic acid analyzed in order to accurately measure the amount of the organic acid originally present in the sample.

As described herein, the amount of oxygen-18 organic acid measured in a processed sample is used to adjust the amount of unlabeled organic acid measured in the processed sample so as to reflect the amount of unlabeled organic acid originally present in the sample. By this manner, any loss of the unlabeled organic acid due to sample processing is corrected by using the oxygen-18 labeled internal standard. The amount of labeled and/or unlabeled organic acid measured following processing may be determined from the mass spectrometry tracing as the peak intensity or the peak area.

In a preferred approach, the step of adjusting the amount of unlabeled organic acid to reflect the starting amount is accomplished by calculating a ratio of unlabeled organic acid measured to oxygen-18 labeled organic acid measured ("unlabeled/labeled OA ratio") and comparing to a standard curve of unlabeled/labeled OA ratio versus unlabeled organic acid concentration. The standard curve is prepared from standard samples containing increasing amounts of unlabeled organic acid and a constant amount of a structurally similar or identical oxygen-18 labeled organic acid, and processed similarly to the samples which are to be adjusted using the standard curve. The standard samples should use the same matrix (e.g., urine, serum, etc.) as the samples to be adjusted based on the standard curve. Thus, if one is determining the amount of an unlabeled organic acid present in human urine, then the standard curve should be prepared using the identical unlabeled organic acid and structurally similar or identical oxygen-18 labeled organic acid prepared in urine. One skilled in the art would appreciate that the results would be the same of the ratio determined from the processed sample and used for the standard curve were labeled/unlabeled OA ratio (as opposed to an unlabeled/labeled OA ratio).

An efficient way of using the standard curve is to derive by linear regression analysis of recorded peak areas or peak intensities using formula I below:

$$y=(a)(c)+b \qquad \text{[formula I]}$$

wherein
y=unlabeled/labeled OA ratio (or vice versa)
a=slope
c=concentration of unlabeled organic acid (from standard)
b=intercept (unlabeled/labeled OA ratio (or vice versa))

Generally, about four or more standard samples containing different and known concentrations of unlabeled organic acid combined with the appropriate labeled internal standard are used to generate a curve preferably using linear regression analysis (see FIG. 11 for an exemplary curve). Formula I reflecting a particular standard curve can be used to calculate the concentration of a sample containing an unknown amount of an organic acid by using formula II below.

$$c = \frac{y-b}{a} \qquad \text{[formula II]}$$

wherein
y=unlabeled/labeled OA ratio (or vice versa)
a=slope
c=concentration of unlabeled organic acid (from unknown sample)
b=intercept (unlabeled/labeled OA ratio (or vice versa))

Using formula II, one inputs as "y" the ratio of unlabeled/labeled OA ratio (or vice versa if the standard curve was vice versa) to obtain a calculated value "c" reflecting the concentration of unlabeled organic acid present in the starting sample. This method of using ratios and constructing standard curves is well known in the art (see Chen et al., Rapid Commun Mass Spectrom, 15:159-163 (2001)).

Other approaches well known in the art can be used to adjust the amount of unlabeled organic acid measured in a processed sample to reflect the starting amount or the organic acid. For example, one may determine a recovery of internal standard oxygen-18 labeled organic acid detected versus the amount added to the sample. This fractional recovery of the internal standard can be used to adjust (upwards, if necessary) the amount of structurally similar to identical unlabeled organic acid in the processed sample to reflect its amount in the starting sample. For example, if the yield of internal standard is 80%, then the amount of structurally similar to identical unlabeled organic acid measured following processing is divided by 0.8 to reflect its amount in the starting sample volume.

In some embodiments, the biological sample can be processed to enrich the organic acid(s) prior to detection. This may involve extraction with solvents, drying, acidification, centrifugation, and the like. Processing also may involve chemically modifying the organic acids to improve their detectability. For example, chemical derivatization of organic acids and oxygen-18 labeled organic acids is required if the GC-MS is used in the detection method. Methods of processing to improve detection of organic acids from a biological sample are well known in art. See, e.g., Kushnir et al., *Clin Chem* 47:1993-2002 (2001); Pitt et al., *Clin Chem* 48: 1970-1980 (2002); Zytkovicz et al., *Clin Chem* 47: 1945-1955 (2001) for organic acid processing and detection by mass spectrometry.

Unlabeled and labeled organic acids may be detected by mass differences using mass spectrometry, and the like. Preferred methods of detection employ mass spectrometry or tandem mass spectrometry.

In a further aspect of the present invention, provided is a method of diagnosing an individual with a metabolic defect characterized by an amount of an organic acid in a body fluid of the individual that is abnormally higher than that present in normal individuals. The method comprises a) adding to a sample from the individual an amount of an oxygen-18 labeled organic acid structurally similar or identical to the unlabeled organic acid to be measured; b) processing the sample; c) measuring the amount of unlabeled organic acid and oxygen-18 organic acid in the processed sample; d) using the amount of oxygen-18 organic acid measured in step c) to adjust the amount of unlabeled organic acid measured in the processed sample so as to reflect the amount of unlabeled organic acid originally present in the sample; and e) determining if the amount of the unlabeled organic acid detected in the sample is an abnormal amount. In a preferred embodiment, if only a single oxygen-18 organic acid is used, the oxygen-18 labeled organic acid is not oxygen-18 labeled homovanillic acid.

In yet a further aspect of the present invention, provided is a method of diagnosing an individual with a metabolic defect characterized by an abnormal amount of at least one unlabeled organic acid in a sample of the individual, said method comprising: a) adding to a sample from the individual an amount of at least one oxygen-18 labeled organic acid selected from each of hydroxy mono-acid, dihydroxy mono-acid, dicarboxyl organic acid, hydroxyl dicarboxyl acid, tricarboxyl acid, glycine conjugate and oxo acid; b) processing the sample; c) measuring the amount of unlabeled organic acids and oxygen-18 organic acids in the processed sample; d) using the amount of an oxygen-18 organic acid measured in step c) to adjust the amount of a structurally similar or identical unlabeled organic acid measured in the processed sample so as to reflect the amount of the at least one unlabeled organic acid originally present in the sample; and e) determining if the amount of the at least one unlabeled organic acid originally present in the sample is an abnormal amount, thereby diagnosing the existence a metabolic defect in the individual.

By "individual" is meant any eukaryotic organism. Preferred organisms are mammals. A preferred mammal is human. An individual can be a patient, which refers to a human presenting to a medical provider for diagnosis or treatment of a disease. The term "individual" includes adults, juvenile and prenatal forms. Particularly preferred subjects are humans with symptoms of metabolic disease.

In another aspect of the present invention, provided are compositions of oxygen-18 labeled organic acids for use as internal standards to quantitatively determine the recovery of a structurally similar or identical organic acid in a sample. The composition comprises at least one oxygen-18 labeled organic acid selected from each of a hydroxyl mono-acid, dihydroxy mono-acid, dicarboxyl organic acid, hydroxyl dicarboxyl acid, tricarboxyl acid, glycine conjugate and oxo-acid. In one embodiment, the composition comprises at least two oxygen-18 organic acids from each of the six groups. In further embodiments, the number of labeled acids from each group in the composition may be 3, 4, 5, 6 and even all from each group disclosed herein. Further compositions are provided which comprise a biological sample along with one or more oxygen-18 labeled organic acids.

DETAILED DESCRIPTION OF THE INVENTION

Figure 1:
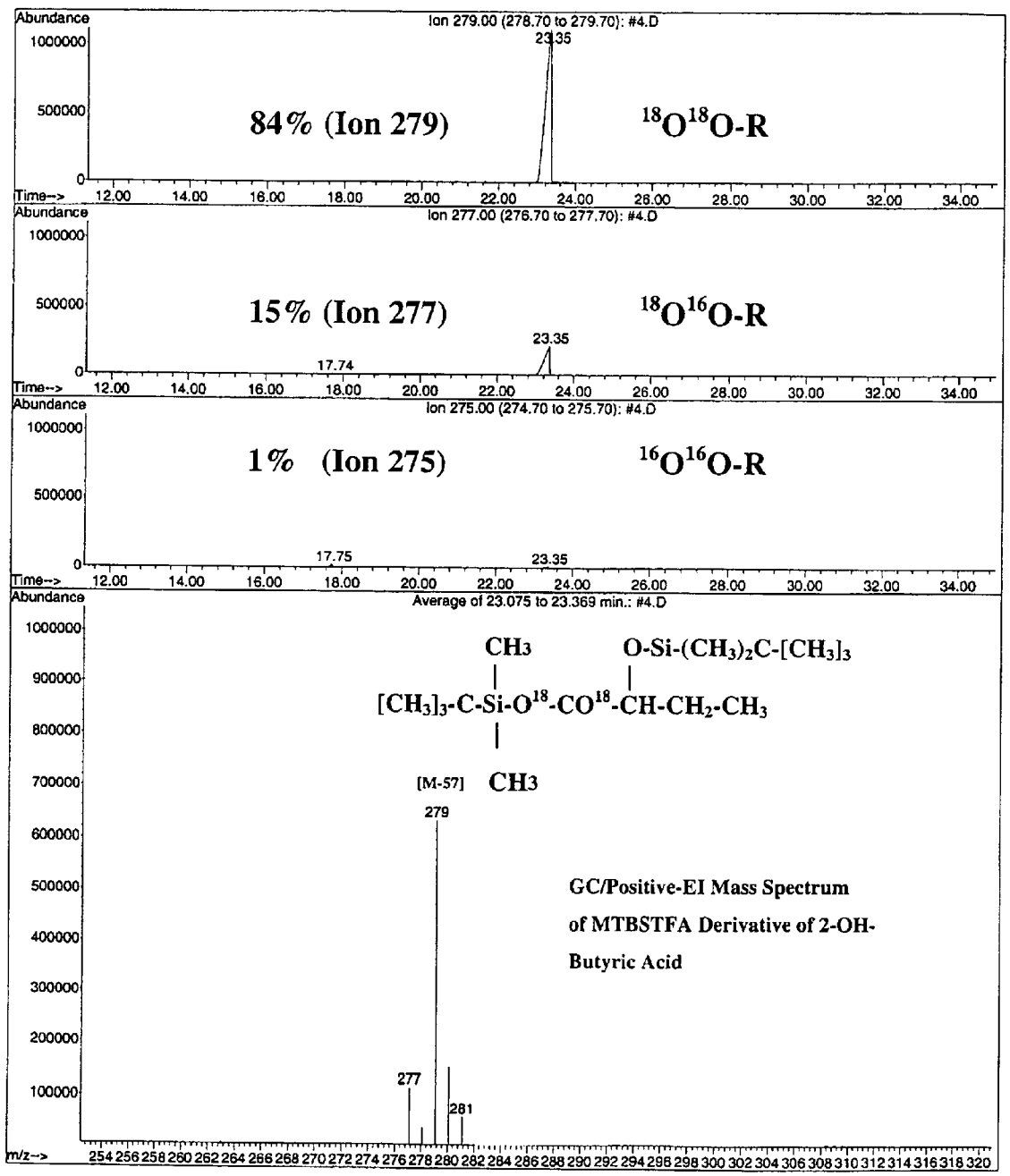
FIG. 1 is a GC/positive-EI mass spectrum of labeled and unlabeled species of 2-OH-butyric acid in a preparation of oxygen-18 labeled 2-OH-butyric acid.

The present invention relates to oxygen-18 labeled organic acids and their use in organic acid quantitation, particularly in quantifying a wide range of organic acids in samples. Accurate quantitation of the amount of organic acids in a sample is important to accurately diagnose the existence of a metabolic defect in an individual. Thus, the present methods are designed to accurately measure the amounts of organic acids by adjusting for losses due to processing required for detection. In one aspect, the invention methods accomplish this by using oxygen-18 radiolabeled organic acids as internal standards for measuring the recovery of the organic acid following processing. The oxygen-18 labeled organic acid used to estimate recovery are structurally similar or identical to the organic acid sought to be analyzed. In a preferred embodiment, the oxygen-18 labeled organic acid used to determine recovery is identical (except for the use of 18 oxygen in place of 16 oxygen) to the organic acid to be quantitated.

Structurally similar organic acids are those that fall within well known groups, including the hydroxyl mono-acids, dihydroxy mono-acids, dicarboxyl organic acids, hydroxyl dicarboxyl acids, tricarboxyl acids, glycine conjugates and oxo acids. The structure of exemplary structurally similar organic acids from each of these groups is provided in Tables 1-7, respectively.

Members comprising the class of hydroxy mono-acids are well known in the art and include, for example, glycolic acid, lactic acid, 3-hydroxypropionic acid, 2-hydroxybutyric acid, 3-hydroxyisobutyric acid, 3-hydroxybutyric acid, 4-hydroxybutyric acid, 2-hydroxyisovaleric acid, 3-hydroxy-2-methylbutyric acid, 3-hydroxy isovaleric acid, 3-hydroxy-2-ethylpropionic acid, 3-hydroxyvaleric acid, 4-hydroxyisovaleric acid, 5-hydroxyhexanoic acid, 2-hydroxyisocaproic acid, 2-hydroxy-3-methylvaleric acid, 5-hydroxyhexanoic acid, 3-hydroxy-2-methylvaleric acid, 2-hydroxyphenylacetic acid, 4-hydroxy phenylacetic acid, 4-hydroxycyclohexylacetic acid, phenyllacetic acid, 4-hydroxyphenylpropionic acid, 5-hydroxyindoleacetic acid, homvanillic acid, indoleacetic acid and 3-hydroxydodecanoic acid. Table 1 contains the chemical structures, molecular formulas, and molecular weights of exemplary hydroxyl mono-acids.

TABLE 1

| Hydroxy Mono-Acids | | | |
| --- | --- | --- | --- |
| Hydroxy Mono-Acids | | | |
| Name | MF | MW | Structure |
| Glycolic | C2H4O3 | 76.02 | HO—C(=O)—CH2—OH |
| Lactic | C3H6O3 | 90.03 | HO—C(=O)—CH(OH)—CH3 |
| 3OH Propionic | C3H6O3 | 90.03 | HO—C(=O)—CH2—CH2—OH |

TABLE 1-continued

Hydroxy Mono-Acids
Hydroxy Mono-Acids

| Name | MF | MW | Structure |
|---|---|---|---|
| 2OH Butyric | C4H8O3 | 104.05 | HO—C(=O)—CH(OH)—CH2—CH3 |
| 3OH Isobutyric | C4H8O3 | 104.05 | HO—C(=O)—CH(CH3)—CH2—OH |
| 3OH Butyric | C4H8O3 | 104.05 | HO—C(=O)—CH2—CH(OH)—CH3 |
| 4OH Butyric | C4H8O3 | 104.05 | HO—C(=O)—CH2—CH2—CH2—OH |
| 2OH Isovaleric | C5H10O3 | 118.06 | HO—C(=O)—CH(OH)—CH(CH3)—CH3 |
| 3OH2Me Butyric | C5H10O3 | 118.06 | HO—C(=O)—CH(CH3)—CH(OH)—CH3 |
| 3OH Isovaleric | C5H10O3 | 118.06 | HO—C(=O)—CH2—C(OH)(CH3)—CH3 |
| 3OH2Et Propionic | C5H10O3 | 118.06 | HO—C(=O)—CH(CH2CH3)—CH2—OH |
| 3OH Valeric | C5H10O3 | 118.06 | HO—C(=O)—CH2—CH(OH)—CH2—CH3 |
| 4OH Isovaleric | C5H10O3 | 118.06 | HO—C(=O)—CH2—CH(CH3)—CH2—OH |
| 5OH Hexanoic | C6H12O3 | 132.08 | HO—C(=O)—CH2—CH2—CH2—CH(OH)—CH3 |
| 2OH Isocaproic | C6H12O3 | 132.08 | HO—C(=O)—CH(OH)—CH2—CH(CH3)—CH3 |
| 2OH3Me Valeric | C6H12O3 | 132.08 | HO—C(=O)—CH(OH)—CH(CH3)—CH2—CH3 |
| 5OH Hexanoic | C6H12O3 | 132.08 | HO—C(=O)—CH2—CH2—CH2—CH(OH)—CH3 |

TABLE 1-continued

| | Hydroxy Mono-Acids | | |
|---|---|---|---|
| | Hydroxy Mono-Acids | | |
| Name | MF | MW | Structure |
| 3OH2MethylVaieric | C6H12O3 | 132.08 | HO–C(=O)–CH(CH3)–CH(OH)–CH2–CH3 |
| 2OH Phen acetic | C8H8O3 | 152.05 | HO–C(=O)–CH2–(2-hydroxyphenyl) |
| 4OH PhanAcetic | C8H8O3 | 152.05 | HO–C(=O)–CH2–(4-hydroxyphenyl) |
| 4OHCyclohexylacetic | C8H14O3 | 158.09 | HO–C(=O)–CH2–(4-hydroxycyclohexyl) |
| Phenyllactic | C9H10O3 | 166.06 | HO–C(=O)–CH(OH)–CH2–phenyl |
| 4OH PhenPropionic | C9H10O3 | 166.06 | HO–C(=O)–CH2–CH2–(4-hydroxyphenyl) |
| 5HIAA | C10H9NO3 | 191.06 | 5-hydroxyindole-3-acetic acid |
| Homovanillic | C9H10O4 | 182.06 | HO–C(=O)–CH2–(3-methoxy-4-hydroxyphenyl) |
| Indotetactic | C11H11NO3 | 205.07 | indol-3-yl–CH2–CH(OH)–C(=O)–OH |
| 3OH Oodecanolc | C12H24O3 | 216.17 | HO–C(=O)–CH2–CH(OH)–(CH2)8–CH3 |

Members comprising the class of dihydroxy mono-acids are well known in the art and include, for example, glyceric acid, mevalonic acid, vanillymandelic acid or 4-hydroxy phenylacetic acid. Table 2 contains the chemical structures, molecular formulas, and molecular weights of exemplary dihydroxy mono-acids.

TABLE 2

Dihydroxy Mono-Acids
Dihydroxy Mono-Acids

| Name | MF | MW | Structure |
|---|---|---|---|
| Glyceric | C2H6O4 | 106.03 | HO—C(=O)—CH(OH)—CH2(OH) |
| Mevalonic | C6H12O4 | 149.07 | HO—C(=O)—CH2—C(OH)(CH3)—CH2—CH2(OH) |
| VMA | C9H10O5 | 198.05 | HO—C(=O)—CH(OH)—C6H3(O—CH3)(OH) |
| 4OH Phenlactic | C9H10O4 | 182.06 | HO—C(=O)—CH(OH)—CH2—C6H4—OH |

Members comprising the class of dicarboxyl organic acids are well known in the art and include, for example, malonic acid, methylmalonic acid, succinic acid, ethylmalonic acid, methylsuccinic acid, glutaric acid, 3-methyl glutaric acid, adipic acid, 3-methyl adipic acid, suberic acid, azelaic acid, sebacic acid or dodecanedioic acid. Table 3 contains the chemical structures, molecular formulas, and molecular weights of exemplary dicarboxyl organic acids below.

TABLE 3

Di-Acids
Di-Acids

| Name | MF | MW | Structure |
|---|---|---|---|
| Malonic | C3H4O4 | 104.01 | HO—C(=O)—CH2—C(=O)—OH |
| MeMalonic | C4H6O4 | 118.03 | HO—C(=O)—CH(CH3)—C(=O)—OH |
| Succinic | C4H6O4 | 118.03 | HO—C(=O)—CH2—CH2—C(=O)—OH |
| Etmalonic | C5H8O4 | 132.04 | HO—C(=O)—CH(CH2—CH3)—C(=O)—OH |
| MeSuccinic | C5H8O4 | 132.04 | HO—C(=O)—CH2—CH(CH3)—C(=O)—OH |

TABLE 3-continued
Di-Acids
Di-Acids
| Name | MF | MW | Structure |
|---|---|---|---|
| Glutaric | C5H8O4 | 132.04 | 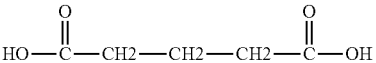 |
| 3Me Glutaric | C6H10O4 | 146.06 | 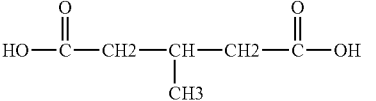 |
| Adipic | C6H10O4 | 146.06 | 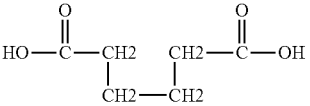 |
| 3Me Adipic | C7H12O4 | 160.07 | 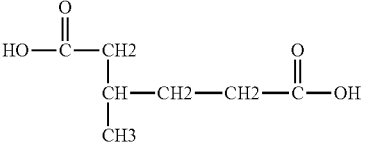 |
| Suberic | C8H14O4 | 174.09 | 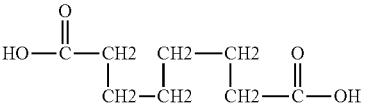 |
| Azelaic | C9H16O4 | 188.10 | 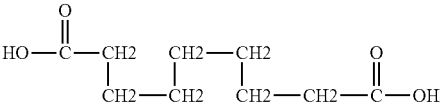 |
| Sebacic | C10H18O4 | 202.12 | 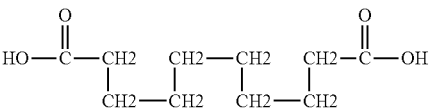 |
| Dodecanedioic | C12H22O4 | 230.15 | 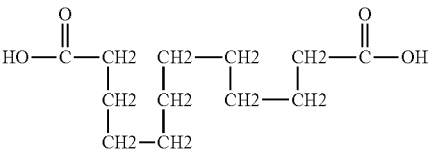 |
| Fumaric | C4H4O4 | 116.01 | 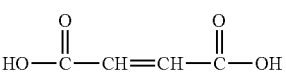 |
| Glutaconic | C5H6O4 | 130.03 | 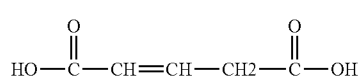 |
| 2Me Glutaconic | C6H8O4 | 144.04 | 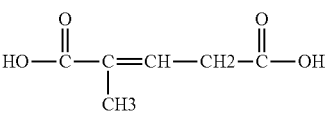 |

TABLE 3-continued

Di-Acids

| Name | MF | MW | Structure |
|---|---|---|---|
| 3Me Glutaconic | C6H8O4 | 194.04 | HO—C(=O)—CH=C(CH3)—CH2—C(=O)—OH |
| Octenedioic | C8H12O4 | 172.07 | HO—C(=O)—CH2(CH=CH)—CH2(CH2)—CH2—C(=O)—OH |

Members comprising the class of hydroxyl dicarboxyl organic acids are well known in the art and include, for example, malic acid, 2-hydroxyglutaric acid, 3-hydroxyglutaric acid, 3-hydroxy-3-methylglutaric acid, 2-hydroxyadipic acid, 3-hydroxyadipic acid or 3-hydroxysebacic acid. Table 4 contains the chemical structures, molecular formulas, and molecular weights of exemplary hydroxyl dicarboxyl organic acids.

TABLE 4

Hydroxyl Dicarboxyl-Acids (Hydroxy Di-Acids)

| Name | MF | MW | Structure |
|---|---|---|---|
| Malic | C4H6O5 | 134.02 | HO—C(=O)—CH2—CH(OH)—C(=O)—OH |
| 2OH Glutaric | C5H8O5 | 148.04 | HO—C(=O)—CH(OH)—CH2—CH2—C(=O)—OH |
| 3OH Glutaric | C5H8O5 | 148.04 | HO—C(=O)—CH2—CH(OH)—CH2—C(=O)—OH |
| 3OH3Me Glutaric | C6H10O5 | 162.05 | HO—C(=O)—CH2—C(CH3)(OH)—CH2—C(=O)—OH |
| 2OH Adipic | C6H10O5 | 162.05 | HO—C(=O)—CH(OH)(CH2—CH2)—CH2—C(=O)—OH |
| 3OH Adipic | C6H10O5 | 162.05 | HO—C(=O)—CH2(CH(OH))—CH2(CH2)—C(=O)—OH |
| 3OHSebacic | C10H18O5 | 218.11 | HO—C(=O)—CH2(CH(OH))—CH2(CH2)—CH2(CH2)—CH2—C(=O)—OH |

Members comprising the class of tricarboxyl organic acids are well known in the art and include, for example, isocitric acid, citric acid, methyl citric acid or aconitic acid. Table 5 contains the chemical structures, molecular formulas, and molecular weights of exemplary tricarboxyl organic acids.

TABLE 5

Tricarboxyl organic acids
Tri-Acids

| Name | MF | MW | Structure |
|---|---|---|---|
| Isocitric | C6H8O7 | 192.03 | HO—C(=O)—CH2—C(HO—C(=O))(H)—CH(OH)—C(=O)—OH |
| Citric | C6H8O7 | 192.03 | HO—C(=O)—CH2—C(HO—C(=O))(OH)—CH2—C(=O)—OH |
| Me Citric | C7H10O7 | 206.04 | HO—C(=O)—CH2—C(HO—C(=O))(HO)—CH(CH3)—C(=O)—OH |
| Aconitic | C6H6O6 | 174.02 | HO—C(=O)—CH2—C(HO—C(=O))=C(H)—C(=O)—OH |

Members comprising the class of glycine conjugate organic acids are well known in the art and include, for example, propionylglycine, crotonylglycine, isobutyrylglycine, butyrylglycine, tiglylglycine, 3-methyl crotonylglycine, 2-methyl butyrylglycine, isovalerylglycine, valerylglycine, hexanoylglycine, hippuric acid, phenpropionylglycine or suberylglycine. Table 6 contains the chemical structures, molecular formulas, and molecular weights of exemplary glycine conjugate organic acids.

TABLE 6

Glycine Conjugate Organic Acids
Glycine Conjugates

| Name | MF | MW | Structure |
|---|---|---|---|
| PropionylGly | C5H9O3N | 131.06 | HO—C(=O)—CH2—N(H)—C(=O)—CH2—CH3 |
| Crotonyl Gly | C6H9O3N | 143.06 | HO—C(=O)—CH2—N(H)—C(=O)—CH=CH—CH3 |

TABLE 6-continued
Glycine Conjugate Organic Acids
Glycine Conjugates
| Name | MF | MW | Structure |
|---|---|---|---|
| IsobutyrylGly | C6H11O3N | 145.07 | 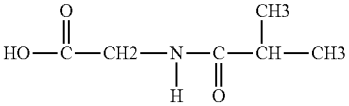 |
| Butyryl Gly | C6H11O3N | 145.07 | 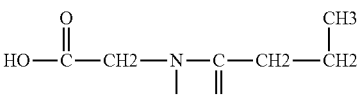 |
| TiglylGly | C7H11O3N | 157.07 | 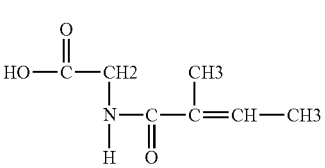 |
| 3Me CrotonylGly | C7H11O3N | 157.07 | 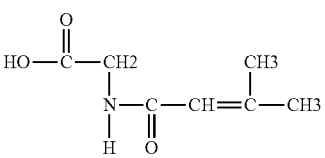 |
| 2Me ButyrylGly | C7H13O3N | 159.09 | 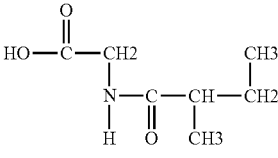 |
| IsovalerylGly | C7H13O3N | 159.09 | 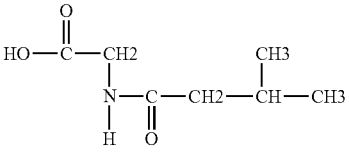 |
| Valeryl Gly | C7H13O3N | 159.09 | 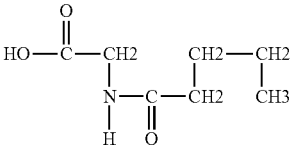 |
| HexanoylGyl | C8H15O3N | 173.10 | 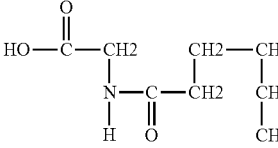 |
| Hippuric | C9H9O3N | 179.06 | 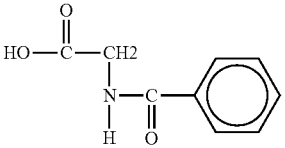 |
| PhenPropionylGly | C11H13O3N | 207.09 | 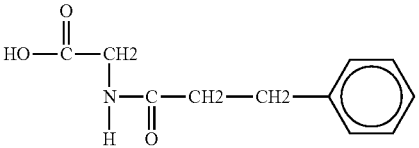 |

TABLE 6-continued

Glycine Conjugate Organic Acids
Glycine Conjugates

| Name | MF | MW | Structure |
|---|---|---|---|
| SuberylGly | C10H17O5N | 231.11 | (structure shown) |

Structure of SuberylGly:

$$HO-\underset{\underset{O}{\|}}{C}-CH_2-\underset{\underset{H}{|}}{N}-\underset{\underset{O}{\|}}{C}-CH_2-CH_2-CH_2-CH_2-CH_2-CH_2-\underset{\underset{O}{\|}}{C}-OH$$

Members comprising the class of oxo acids are well known in the art and include, for example, glyoxlic acid, pyruvic acid, 2-oxobutyric acid, acetoacetic acid, 2-oxoisovaleric acid, 5-oxoproline, 2-oxo-3-methylvaleric acid, 2-oxoIsocaproic acid, 2-oxoglutaric acid, succinylacetone, 2-oxoadipic acid, 3-oxoadipic acid, phenpyruvic acid, 4-hydroxy phenpyruvic acid or 2-methyl acetoacetic acid. Table 7 contains the chemical structures, molecular formulas, and molecular weights of exemplary oxo acids which include many alpha-keto acids.

TABLE 7

Oxo Acids
Oxo Acids

| Name | MF | MW | Structure |
|---|---|---|---|
| Glyoxlic | C2H2O3 | 74.00 | H—C(=O)—C(=O)—OH |
| Pyruvic | C3H4O3 | 88.02 | CH3—C(=O)—C(=O)—OH |
| 2OxoButyric | C4H6O3 | 102.03 | CH3—CH2—C(=O)—C(=O)—OH |
| AcetoAcetic | C4H6O3 | 102.03 | CH3—C(=O)—CH2—C(=O)—OH |
| 2OxoIsovaleric | C5H8O3 | 116.05 | CH3—CH(CH3)—C(=O)—C(=O)—OH |
| 5Oxo Proline | C5H7O3N | 129.04 | O=C—NH—CH(—C(=O)—OH)—CH2—CH2 (ring) |
| 2Oxo3MeValeric | C6H10O3 | 130.06 | CH3—CH2—CH(CH3)—C(=O)—C(=O)—OH |
| 2OxoIsoCaproic | C6H10O3 | 130.06 | CH3—CH(CH3)—CH2—C(=O)—C(=O)—OH |
| 2OxoGlutaric | C5H6O5 | 146.02 | HO—C(=O)—CH2—CH2—C(=O)—C(=O)—OH |
| SuccAcetone | C7H10O4 | 158.06 | HO—C(=O)—CH2—CH2—C(=O)—CH2—C(=O)—CH3 |
| 2OxoAdipic | C6H8O5 | 160.04 | HO—C(=O)—CH2—CH2—CH2—C(=O)—C(=O)—OH |

TABLE 7-continued

Oxo Acids
Oxo Acids

| Name | MF | MW | Structure |
|---|---|---|---|
| 3OxoAdipic | C6H8O5 | 160.04 | HO-C(=O)-CH2-CH2-C(=O)-CH2-C(=O)-OH |
| PhenPyruvic | C9H8O3 | 164.05 | C6H5-CH2-C(=O)-C(=O)-OH |
| 4OHPhenPyruvic | C9H8O4 | 180.04 | HO-C6H4-CH2-C(=O)-C(=O)-OH |
| 2MeAcetoAcetic | C5H8O3 | 116.06 | CH3-C(=O)-CH(CH3)-C(=O)-OH |

Oxygen-18 labeled organic acids can be prepared using methods previously described for the preparation of oxygen-18-amino acids. K. C. Clay and R. C. Murphy, in Biomedical Mass Spectrometry, Vol. 7, 345 (1980). Generally, the exchange with oxygen-18 water may be carried out under acidic conditions at room temperature for about two-week time.

It has been found herein that use of oxygen-18 labeled organic acids as internal standards increases the accuracy of the assay over other labeled standards such as deuterium-containing organic acids because oxygen-18 labeled organic acids have a much greater mass differential than dueterated organic acid internal standards. Furthermore, one may vary the molecular weight difference between oxygen-18 labeled organic acids and their unlabeled counterparts (oxygen-16 containing-organic acids) by controlling the number of oxygen atoms in the organic acids that become substituted. For example, there is a 4-mass unit difference between oxygen-18 labeled mono acids and oxygen-16 mono acids if both oxygen atoms in the mono carboxylic acid are oxygen-18 atoms. There is a 8-mass unit difference between oxygen-18 labeled dicarboxyl acids and oxygen-16 dicarboxyl acids if both oxygen atoms in each of the carboxylic acid groups are oxygen-18 atoms. Finally, there is a 12-mass unit difference between oxygen-18 labeled tricarboxyl acids and oxygen-16 labeled tricarboxyl acids, if both oxygen atoms in each of the carboxcylic acid groups are oxygen-18 atoms. Thus, depending on the extent of substitution for more complex organic acids, the user may chose a 4 to 12 mass differences in order to reduce the isotopic interfering.

Oxygen-18 being a non-radioactive atom is safer to work with than prior radioactive standards such as tritium-labeled organic acids. As demonstrated herein, oxygen-18 labeled organic acids are relatively stable (i.e. not subject to significant degradation) when mixed with a typical sample such as urine and subjected to processing and analysis of the sample.

Generally, prior to mass spectrometry detection, biological samples undergo extensive processing to enrich the organic acid sought to be detected and then to improve its detectability in the GC analysis system used. Processing may involve extraction, chemical derivitization, and analysis including chromatorgraphy and mass spectrometry, and the like. Extraction of organic acids from biological samples using ethyl acetate is preferred. Chromatography methods such as capillary gas chromatography for processing to separate derivatized organic acids in a biological sample is well known in art. See, e.g., Kushnir et al., Clin Chem 47:1993-2002 (2001); Pitt et al., Clin Chem 48: 1970-1980 (2002); Zytkovicz et al., Clin Chem 47: 1945-1955 (2001) for organic acid processing and detection by mass spectrometry.

In other embodiments, organic acids in a sample, which may or may not have been extracted, can be derivatized in order to improve volatility for organic acid separation by GC. Common derivatization techniques mainly include: (a) preparation of the methyl esters of organic acids using BF3/methanol or diazomethane, (b) preparation of trimethylsilyl derivatives of organic acids using trimethylsilyl reagents and, (c) preparation of Methyl-(tert-butyldimethylsilyl)-derivatives of organic acids using N-methyl-N-(tert-butyldimethylsilyl-trifluoroacetamide. The latter approach is preferred.

Unlabeled organic acid(s) in the sample and oxygen-18 organic acids may be separated and detected by published methods known in the art. A preferred method for organic acid quantitative assay employs GC-MS.

The following examples serve to illustrate the present invention. These examples are in no way intended to limit the scope of the invention.

EXAMPLES

Example 1

GC-MS Analyses of Methyl-(tert-butyldimethylsilyl)-Derivatives of Oxygen-18 labeled Organic Acids Experiments were performed on a GC-Quadrapole mass spectrometer (HP-6890, Series II and 5973 Series mass detector, Hewlett-Packard Co. USA). The oxygen-18 labeled sample in a test tube was dried first under a stream of nitrogen gas, and then 120 μl of a mixture of N-methyl-N-(tert-butyldimethylsilyl-trifluoroacetamide and acetonitrile (1:1; v/v) was added to the tube for the derivatization of the labeled organic acid at 60° C. for 30 minutes. The derivatized sample was then injected into the GC-MS system with an autosampler using the following analytical conditions: (i) a capillary column (Restek-200; 20 m×0.4 µm); (ii) 0.6 mL/min. flow rate, and an initial column temperature at 80° C. and increasing the temperature of the column by 3° C./minute up to a maximum of 260° C.; (iii) mass range from 50 to 700, and the positive electro impact ionization. The peak areas or intensities of ions ([M-57]$^+$) of the derivatized oxygen-18-containing organic acids, generated by GC/MS analysis, were used to determine the percentage or yields of the oxygen-18 labeled organic acids.

Example 2

Labeling and Gas Chromatography-Mass Spectrometric Analysis of the Representatives of Oxygen-18 labeled Hydroxy Mono-Acids The exchange of oxygen-18 with Oxygen-16 within organic acid molecules was carried out by dissolving in a mixture of 100 µl of $H_2^{18}O$ (>95.5%) and 8 µl of 12N-Hydrocholoride acid, and maintaining at room temperature for 3, 7 and 14 days, respectively. The percentage (yields) of oxygen-18 labeled organic acids at 3, 7 and 14 days were determined by comparing the peak areas or peak intensities of methyl-(tert-butyldimethylsilyl)-derivatives of the $^{18}$O-containing organic acids analyzed by GC-MS.

The 3-day and 7-day labeling incubation resulted in 76% yield of double oxygen-18 labeled 2-hydroxy butyric acid, while the 15-day incubation resulted in a 84% yield. When the 15 day incubation was analysed by the GC/MS method, a peak at m/z 279 (mass/charge) in the spectrum was obtained corresponding to the double oxygen-18 labeled 2-hydroxy butyric acid while the mono oxygen-18 labeled and the unlabeled 2-hydroxy butyric acid molecules gave ions at m/z 277 and 275, respectively (FIG. 1). The results showed that both carbonyl oxygen atoms in 2-hydroxy butyric acid were exchanged for oxygen-18 isotopes, because there was a difference of 4 atomic mass units between the labeled (at m/z 279) and unlabeled (at m/z 275) acids.

Figure 2:
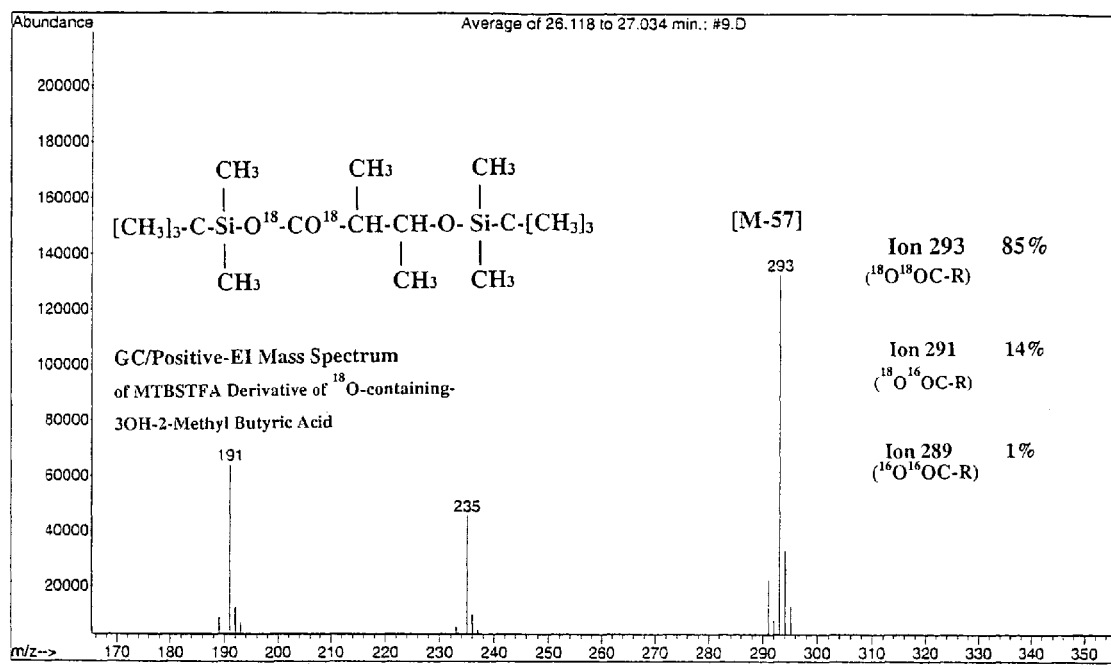
FIG. 2 is a GC/positive-EI mass spectrum of labeled and unlabeled species of 3-OH-2-methyl butyric acid in a preparation of oxygen-18 labeled 3-OH-2-methyl butyric acid.
Figure 3:
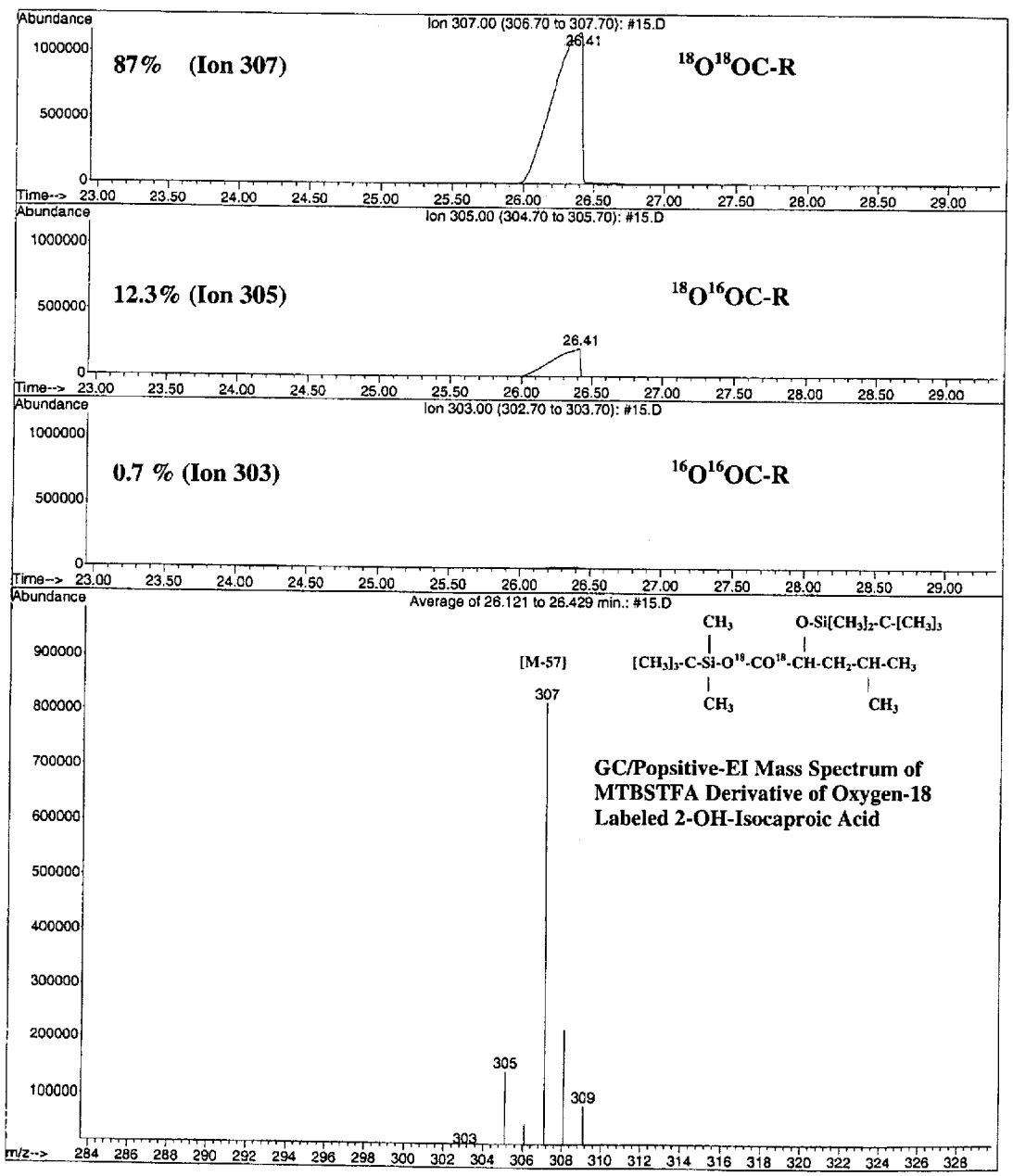
FIG. 3 is a GC/positive-EI mass spectrum of labeled and unlabeled 2-OH-isocaproic acid in a preparation of oxygen-18 labeled 2-OH-isocaproic acid.
Figure 4:
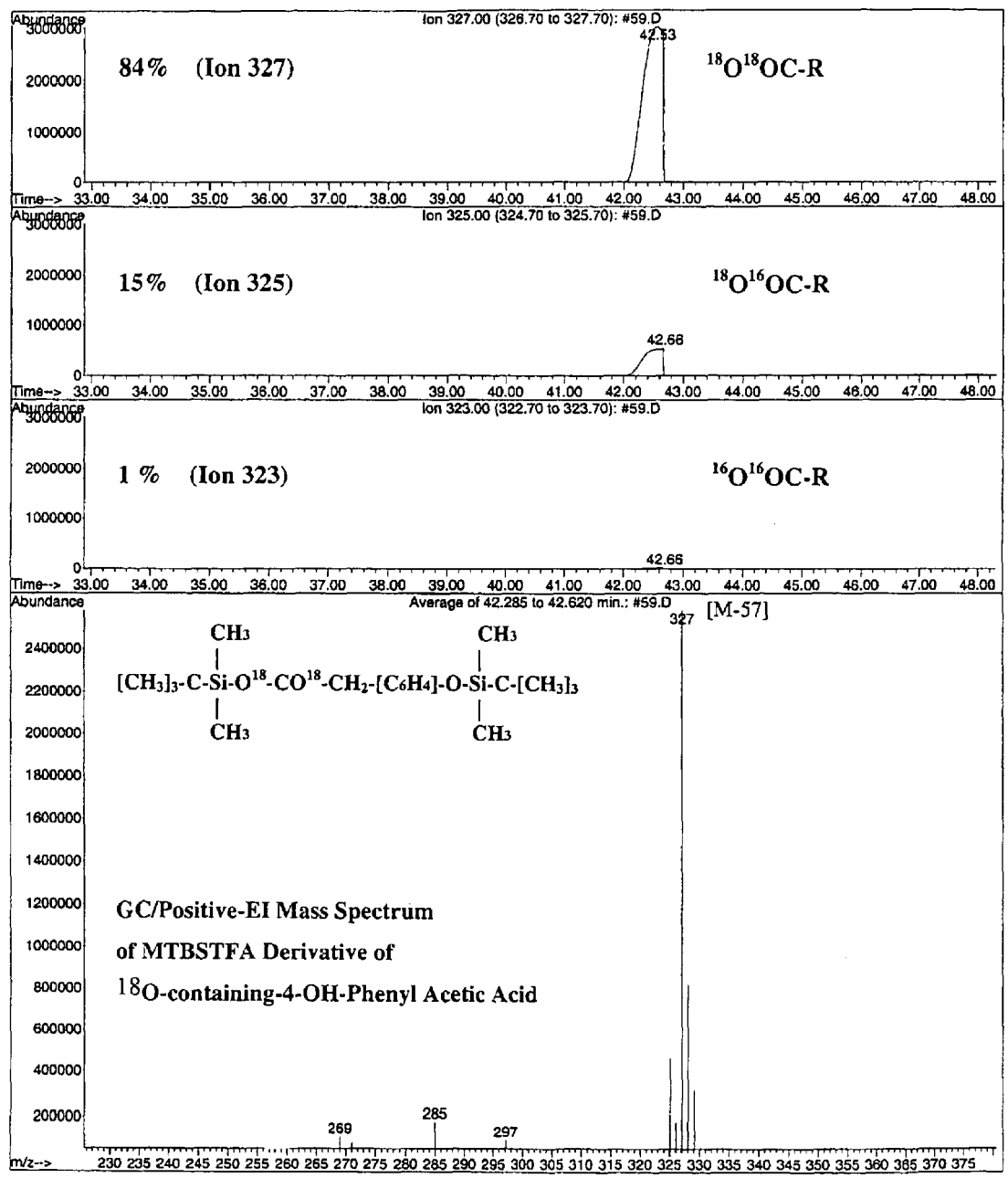
FIG. 4 is a GC/positive-EI mass spectrum of labeled and unlabeled 4-OH-phenyl acetic acid in a preparation of oxygen-18 labeled 4-OH-phenyl acetic acid.

The GC/MS mass spectra of Methyl-(tert-butyldimethylsilyl)-derivatives and yields of other oxygen-18 labeled mono acids including 3-hydroxy-2-methyl butyric acid, 2-OH-Isocaproic acid and 4-hydroxy-phenylacetic acid (15-day incubated products) are shown in FIGS. 2, and 3 and 4, respectively.

Example 3

Figure 5:
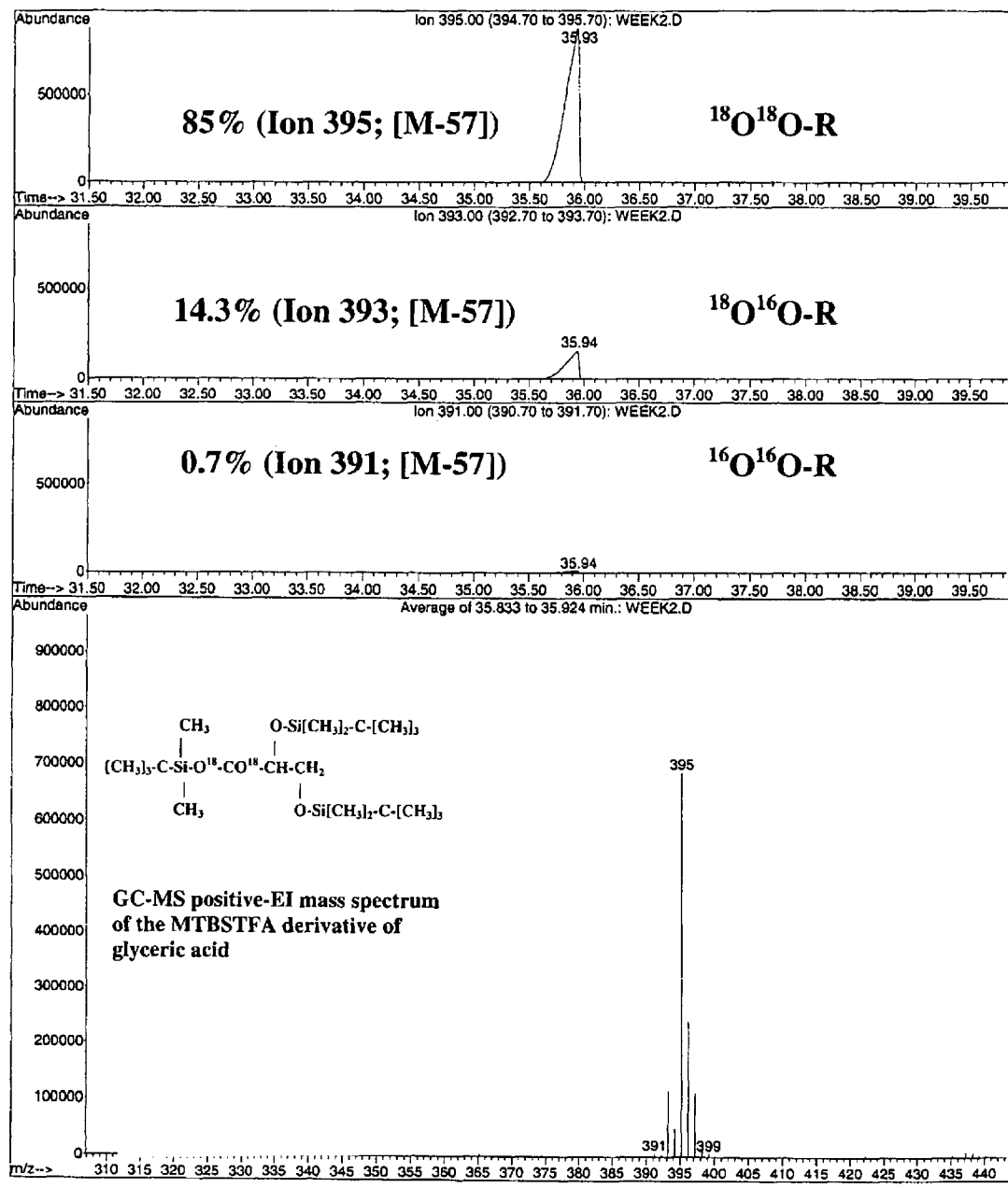
FIG. 5 is a GC/positive-EI mass spectrum of labeled and unlabeled glyceric acid in a preparation of oxygen-18 labeled glyceric acid.

Labeling and Gas Chromatography-Mass Spectrometric Analysis of the Representatives of Oxygen-18 Labeled Di-Hydroxy Mono-Acids Glyceric acid was labeled with oxygen-18 essentially as described in Example 2. A 3-day incubation gave a 68% yield of double oxygen-18 labeled glyceric acid, a 7-day incubation gives a 80% yield, and a 15-day incubation gave a 85% yield. When the 15-day incubated glyceric acid was analyzed by GC-MS, a peak at m/z 395 in the mass spectrum was observed for the di-oxygen-18 labeled glyceric acid, compared to the mono-labeled and unlabeled glyceric acid, showed ions at m/z 393 and 391, respectively (FIG. 5). The results showed that two oxygen atoms of a carboxyl acid group in glyceric acid were exchanged for oxygen-18, because there was a difference of 4 mass units between the full labeled (at m/z 395) and unlabeled (at m/z 391) acids.

Example 4

Figure 6:
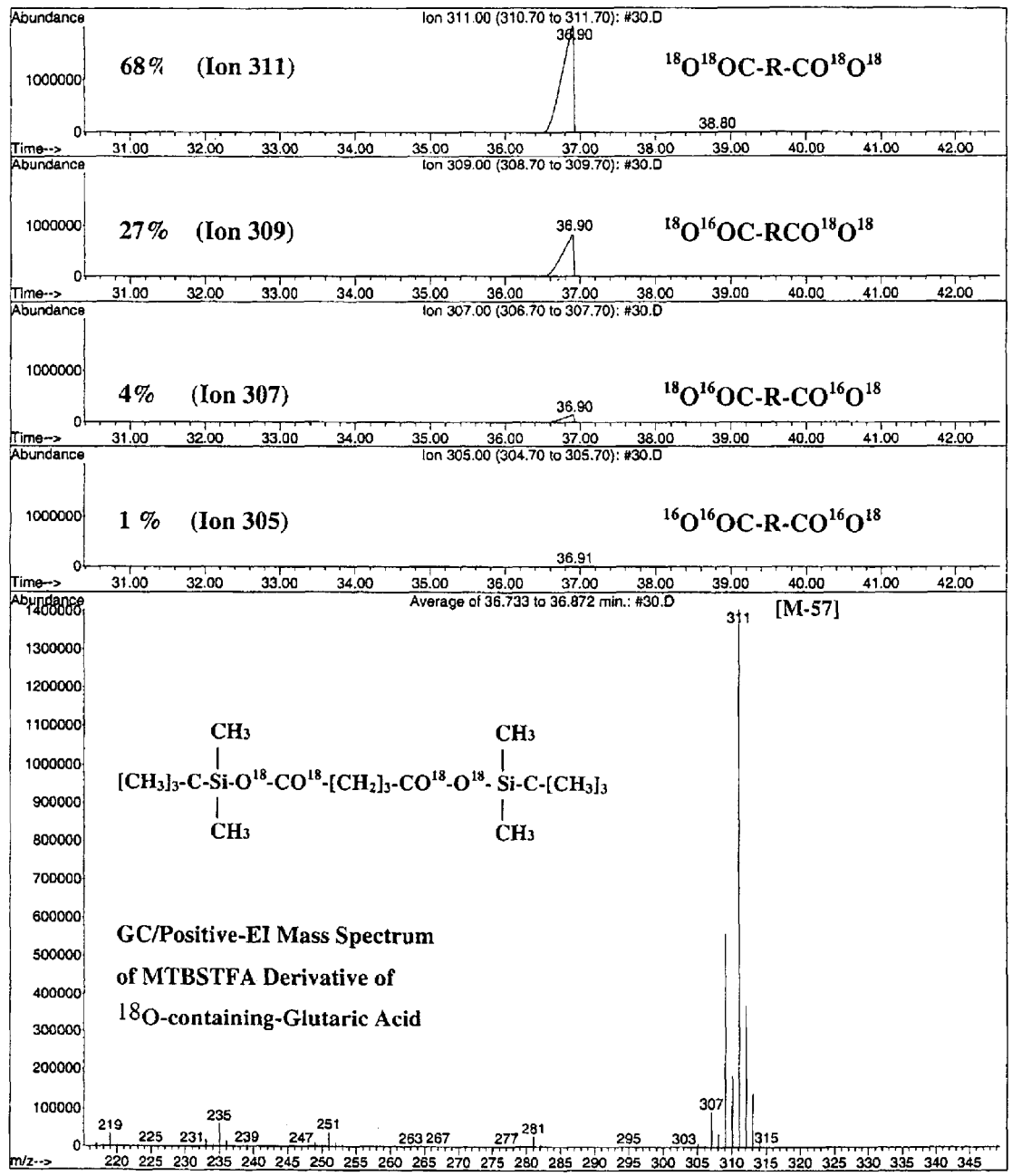
FIG. 6 is a GC/positive-EI mass spectrum of labeled and unlabeled glutaric acid in a preparation of oxygen-18 labeled glutaric acid.

Labeling and Gas Chromatography-Mass Spectrometric Analysis of the representatives of Oxygen-18 labeled Di-Acids Glutaric acid was labeled with oxygen-18 essentially as described in Example 2. A 3-day incubation gave a 60% yield of quadruple oxygen-18 labeled glutaric acid, a 7-day incubation gave a 62% yield, and a 15-day incubation gave a 68% yield. When the 15-day incubated glutaric acid was measured using the GC-MS method, a peak at m/z 311 in the mass spectrum relates to the quadruple labeled glutaric acid, compared to the tri-, di- and mono-labeled glutaric acid, showed ions at m/z 309, 307 and 305, respectively (FIG. 6). The results showed that four oxygen atoms of the two carboxyl acid groups in glutaric acid molecule were exchanged for oxygen-18, because there was a difference of 8 mass units between the full labeled (at m/z 311) and the unlabeled (at m/z 303) acids.

Example 5

Figure 7:
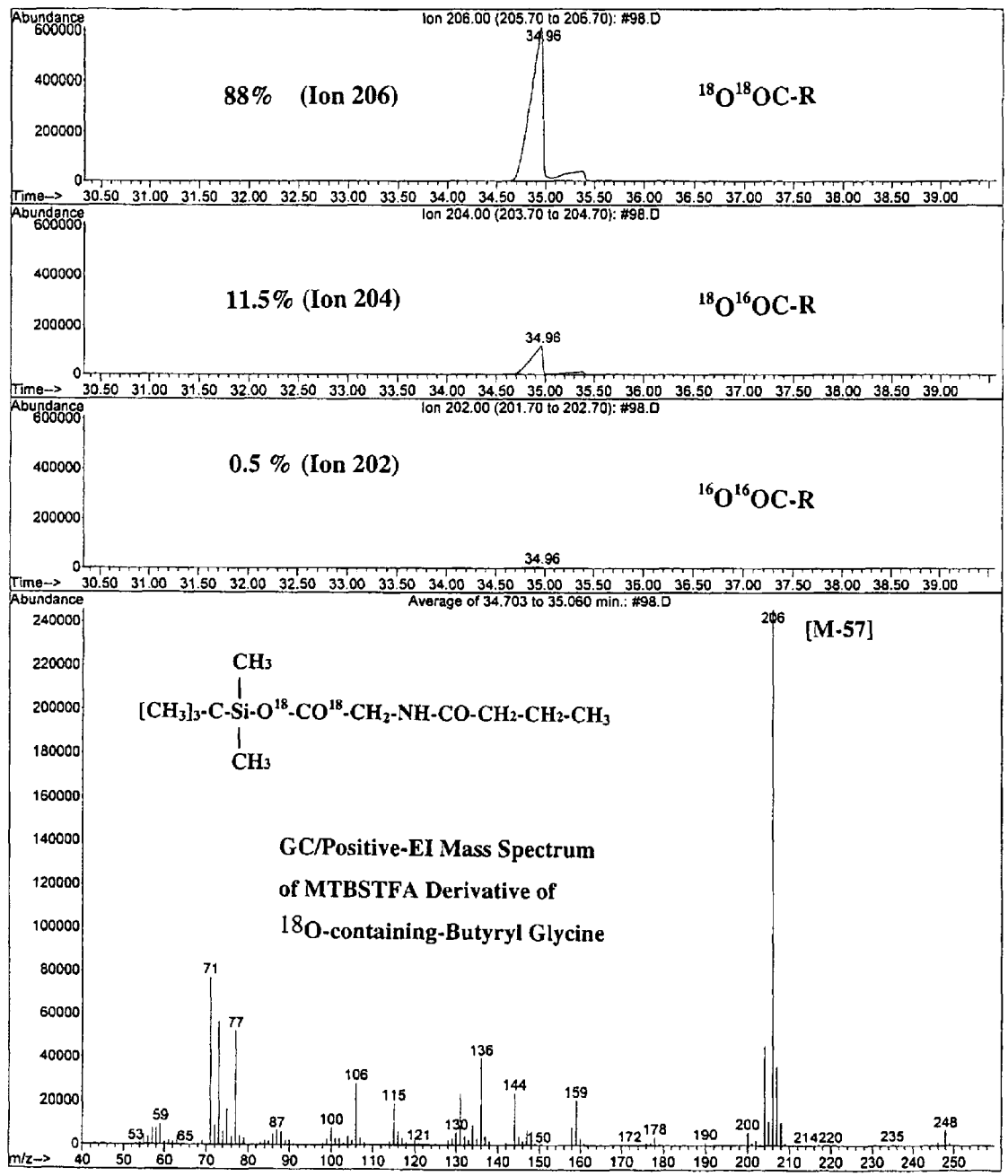
FIG. 7 is a GC/positive-EI mass spectrum of labeled and unlabeled butyryl glycine in a preparation of oxygen-18 labeled butyryl glycine.

Labeling and Gas Chromatography-Mass Spectrometric Analysis of the representatives of Oxygen-18 Conjugated Glycines Butyryl glycine was labeled with oxygen-18 essentially as described in Example 2. A'3-day incubation gives a 76% yield of double oxygen-18 labeled butyryl glycine, and both 7-day and 15-day incubations give approximately 88% yield. When the 15-day incubated butyryl glycine was measured using the GC-MS method, a peak at m/z 206 corresponds to the double labeled Butyryl glycine, compared with the mono-labeled and unlabeled Butyryl glycine, shown at m/z 204 and 202 (FIG. 7). The results showed that two oxygen atoms in carboxyl acid group of Butyryl glycine molecule were exchanged for oxygen-18, because there was a difference of 4 mass units between the fully labeled (at m/z 206) and the unlabeled (at m/z 202) Butyryl glycine.

Figure 8:
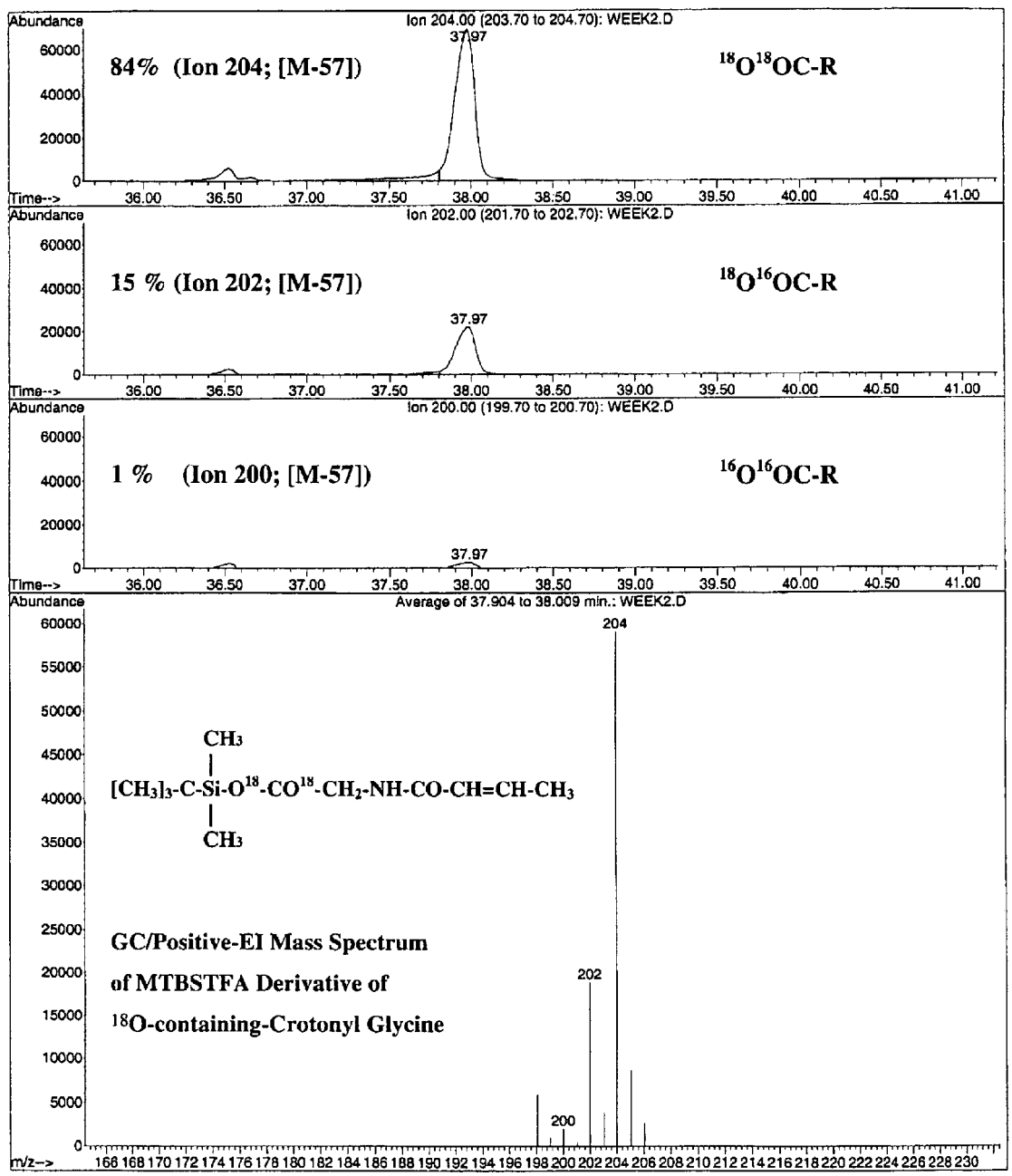
FIG. 8 is a GC/positive-EI mass spectrum of labeled and unlabeled crotonyl glycine in a preparation of oxygen-18 labeled crotonyl glycine.

The GC/MS mass spectrum of methyl-(tert-butyldimethylsilyl)-derivative and yields of other oxygen-18 labeled crotonyl glycine (a 15-day incubated product) is also shown in FIG. 8.

Example 6

Figure 9:
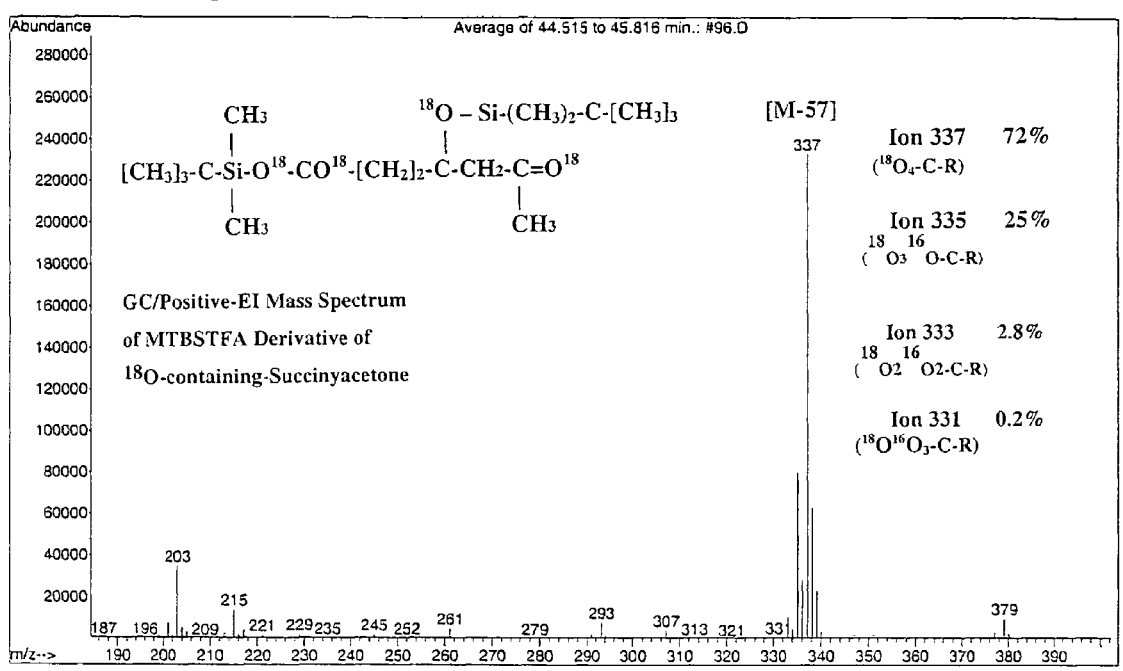
FIG. 9 is a GC/positive-EI mass spectrum of labeled and unlabeled succinyacetone in a preparation of oxygen-18 labeled succinyacetone.

Labeling and Gas Chromatography-Mass Spectrometric Analysis of the representatives of Oxygen-18 2-Oxo-Acids Succinyacetone was labeled with oxygen-18 essentially as described in Example 2. A 3-day incubation gave a 50% yield of quintuple oxygen-18 labeled succinyacetone, and both 7-day and 15-day incubations gave a 72% yield. When the 15-day incubated succinyacetone was measured using GC-MS, an ion peak at m/z 337 in the spectrum was observed for the quintuple labeled succinyacetone, compared to the tri-, di- and mono-labeled succinyacetone, which showed ions at m/z 335, 333 and 331, respectively (FIG. 9). The results showed that four oxygen atoms in the compound were exchanged for oxygen-18 isotopes, because there is was a difference of 8 atomic mass units between the fully labeled (at m/z 337) and the unlabeled (at m/z 329) compound.

Figure 10:
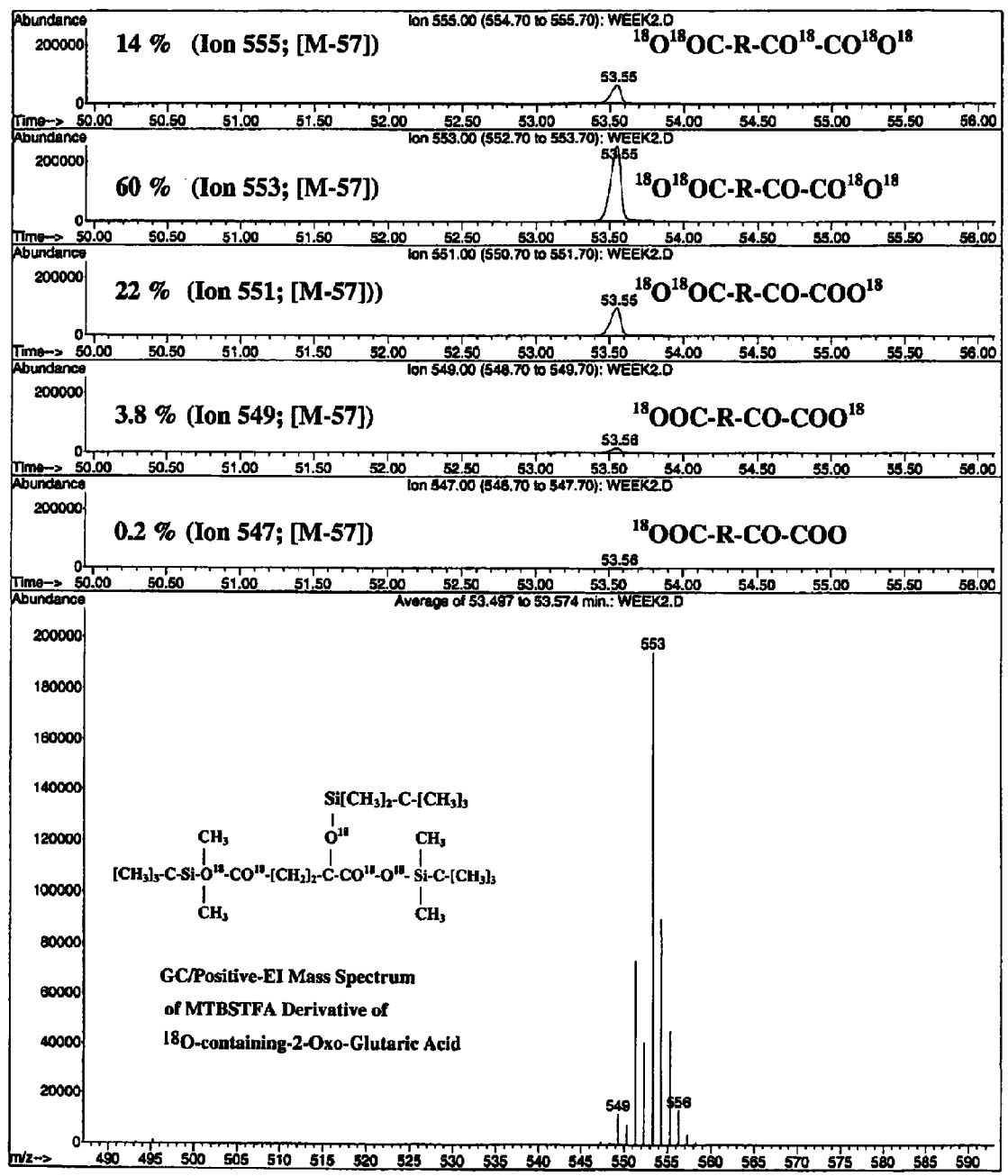
FIG. 10 is a GC/positive-EI mass spectrum of labeled and unlabeled 2-oxo-glutaric acid in a preparation of oxygen-18 labeled 2-oxo-glutaric acid.

The GC/MS mass spectrum of methyl-(tert-butyldimethylsilyl)-derivative and yields of other oxygen-18 labeled 2-Oxo-glutaric acid (a 15-day incubated product) are also shown in FIG. 10.

Example 7

Stability of Oxygen-18—Containing Organic Acids

The stability of oxygen-18 labeled organic acids in the sample preparation procedure was evaluated. The following steps were performed: 1) 50 microliters (μL) of normal human urine and 10 μL of oxygen-18 labeled organic acid were added to 1.440 milliliters (mL) of water; 2) The pH was adjusted to 1 with 1N sulfuric acid; 3) 2 mL of ethyl-acetate was added to the solution, followed by shaking for 10 minutes; 4) the upper phase solvent was transferred to a new tube, and steps 3 and 4 were repeated at least three times; 5) the transferred solvent was dried under a stream of nitrogen gas; 6) 120 μL of MTBSTFA was added to make the derivatization of the acids at 60° C. for 30 minutes for gas chromatography-mass spectrometric (GC/MS) analysis; and 7) the derivatized sample was injected into a GC/MS instrument (Hewlett-Packard 6890 Series II and 5973 Series mass detector available from Hewlett-Packard Co.) under the following conditions: using a capillary column (Restek-200; 20 m×0.4 μm), having a 0.6 mL/min. flow rate, having an initial column temperature of 80° C. and increasing the temperature of the column by 3° C./minute up to a maximum of about 260° C., using the mass range from 50 to 700, and the mode being positive ion electro impact ionization. The peak areas or peak intensities of ions ([M-57$^+$]) of derivatized oxygen-18-containing organic acids generated by GC/MS analysis were used to determine the approximate recovery of the oxygen-18 labeled organic acids.

Oxygen-18 labeled organic acids, subjected to the process in Example 1, exhibited stability when subject to mass spectrometric analysis. For example, 2-hydroxy-butyric acid, a representative of the 3 and 4 carbon-containing hydroxyl mono-acids, was double (Oxygen-18×2) and single (Oxygen-18×1) labeled with oxygen-18, and both the labeled and unlabeled forms were tested for stability. Both labeled and unlabeled forms of the acid exhibited stability prior to liquid/liquid (L/L) extraction, during an 80 minute L/L extraction, and during a 120 minute L/L extraction are shown in Table 8.

TABLE 8

Stability of oxygen-18-containing 2-OH Butyric Acid

| | Before L/L extraction | L/L 80 min. extraction | L/L 120 min. extraction |
|---|---|---|---|
| Double labeled | 84% | 83% | 80% |
| Single labeled | 15% | 17.4% | 19.7% |
| Unlabeled | 1% | 0.11% | 0.3% |

3-hydroxy-2-methyl butyric acid, a representative of the 5 carbon-containing hydroxyl mono-acids, was double (Oxygen 18×2) and single (Oxygen 18×1) labeled with oxygen-18, and was tested for stability. The labeled acid exhibited stability prior to liquid/liquid (L/L) extraction, during an 80 minute L/L extraction, and during a 120 minute L/L extraction as shown in Table 9.

TABLE 9

Stability of Oxygen-18-Containing 3-Hydroxy-2-Methyl Butyric Acid

| | Before L/L extraction | L/L 80 min. extraction | L/L 120 min. extraction |
|---|---|---|---|
| Double labeled | 85% | 85% | 85% |
| Single labeled | 14.9% | 14.9% | 14.7% |
| Unlabeled | 0.1% | 0.1% | 0.3% |

2-hydroxy isocaproic acid, a representative of the 6 carbon-containing hydroxy mono-acids, was double (Oxygen 18×2) and single (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction are shown in Table 10.

TABLE 10

Stability of Oxygen-18-Containing 2-Hydroxy Isocaproic Acid

| | Before L/L extraction | L/L 80 min. extraction | L/L 120 min. extraction |
|---|---|---|---|
| Double labeled | 84% | 83% | 79% |
| Single labeled | 15.6% | 16.5% | 20.6% |
| Unlabeled | 0.4% | 0.5% | 0.4% |

4-hydroxy phenyl acetic acid, a representative of the 8 through 10 carbon-containing hydroxyl mono-acids, was double (Oxygen 18×2) and single (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction as shown in Table 11.

TABLE 11

Stability of Oxygen-18-Containing 4-Hydroxy Phenyl Acetic Acid

| | Before L/L extraction | L/L 80 min. extraction | L/L 120 min. extraction |
|---|---|---|---|
| Double labeled | 83.7% | 81% | 78% |
| Single labeled | 15.5% | 15.8% | 19.7% |
| Unlabeled | 0.8% | 3.2% | 2.3% |

Glyceric acid, a representative of the 3 through 6 carbon-containing di-hydroxyl mono-acids, was double (Oxygen 18×2) and single (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction as shown in Table 12.

TABLE 12

Stability of Oxygen-18-Containing Glyceric Acid

| | Before L/L extraction | L/L 80 min. extraction | L/L 120 min. extraction |
|---|---|---|---|
| Double labeled | 87% | 84% | 81% |
| Single labeled | 13% | 15.5% | 17.6% |
| Unlabeled | 0% | 0.5% | 2.4% |

Butyryl glycine, a representative of the glycine conjugates, was double (Oxygen 18×2) and single (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction as shown in Table 13.

TABLE 13

Stability of Oxygen-18-Containing Butyryl Glycine

|  | Before L/L extraction | L/L 80 min. extraction | L/L 120 min. extraction |
| --- | --- | --- | --- |
| Double labeled | 85% | 85% | 83% |
| Single labeled | 14.5% | 14.8% | 16.2% |
| Unlabeled | 0.5% | 0.2% | 0.8% |

Crotonyl glycine, a glycine conjugate, was double (Oxygen 18×2) and single (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction as shown in Table 14.

TABLE 14

Stability of Oxygen-18-Containing Crotonyl Glycine

|  | Before L/L extraction | L/L 80 min. extraction | L/L 120 min. extraction |
| --- | --- | --- | --- |
| Double labeled | 84% | 85% | 81% |
| Single labeled | 15.5% | 14.8% | 17.4% |
| Unlabeled | 0.1% | 0.2% | 1.6% |

Glutaric acid, a di-acid, was quintuple (Oxygen 18×4), tri- (Oxygen 18×3), di (Oxygen 18×2) and mono- (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction as shown in Table 15.

TABLE 15

Stability of Oxygen-18-Containing Glutaric Acid

|  | Before L/L extraction | L/L 80 min. extraction | L/L 120 min. extraction |
| --- | --- | --- | --- |
| Oxygen 18 × 4 | 69% | 68% | 65% |
| Oxygen 18 × 3 | 27% | 28% | 30% |
| Oxygen 18 × 2 | 3.5% | 3% | 4% |
| Oxygen 18 × 1 | 0.4% | 0.8% | 0.8% |
| Unlabeled | 0.1% | 0.2% | 0.2% |

Succinyacetone, a Oxo-acid, was quintuple (Oxygen 18×4), tri- (Oxygen 18×3), di (Oxygen 18×2) and mono- (Oxygen 18×1) labeled with oxygen-18, and was tested for stability. Oxygen-18 labeled acid exhibited stability prior to liquid/liquid (L/L) extraction, during an 80 minute L/L extraction, and during a 120 minute L/L extraction as shown in Table 16.

TABLE 16

Stability of Oxygen-18-Containing Succinyacetone

|  | Before L/L extraction | L/L 80 min. extraction | L/L 120 min. extraction |
| --- | --- | --- | --- |
| Oxygen 18 × 4 | 72% | 70% | 67% |
| Oxygen 18 × 3 | 25% | 27% | 29% |
| Oxygen 18 × 2 | 2.8% | 2.8% | 3% |

TABLE 16-continued

Stability of Oxygen-18-Containing Succinyacetone

|  | Before L/L extraction | L/L 80 min. extraction | L/L 120 min. extraction |
| --- | --- | --- | --- |
| Oxygen 18 × 1 | 0.2% | 0.2% | 0.8% |
| Unlabeled | 0% | 0% | 0.2% |

Example 8

Use of Oxygen-18 Labeled Organic Acid as Internal Standard in Quantitatively Analyzing an Organic Acid in Human Urine Samples A potential method for quantitatively analyzing an organic acid in human urine (spiked known amounts of organic acids to normal human urine as 'biological samples") using Oxygen-18 labeled organic acid as internal standard is described below. The experimental procedure including liquid/liquid extraction of organic acids from biological samples, chemical derivatization of purified organic acids, and GC-MS analysis of derivatized organic acids was performed as described in Example 7 with additional details below.

Experimental Procedures:

Step-1: the preparation of calibration standard solutions, pooled quality controls and "biological samples" (spiked known amounts of an organic acid into normal human urine): Calibration standard solutions of 2-Oxo glutaric acid were prepared in human urine at concentrations of 10, 20, 100, 200 and 600 nMol/mL. Pooled quality controls were prepared in human urine at concentrations of 25 and 500 nMol/mL. Finally, 50 and 200 nMol/mL of 2-Oxo glutaric acid were spiked into human urine as "biological samples" in order to tentatively evaluate the method. A constant amount of oxygen-18 labeled 2-Oxo glutaric acid was added to the above solutions and used as internal standard.

Step-2: sample extraction, chemical derivatization and GC-MS analysis (as shown in Example 7);

Step-3: the preparation of calibration curve(s) for quantitatively analyzing an organic acid(s) in human urine samples;

Step-4: Calculation of the result and data evaluation.

Figure 11:
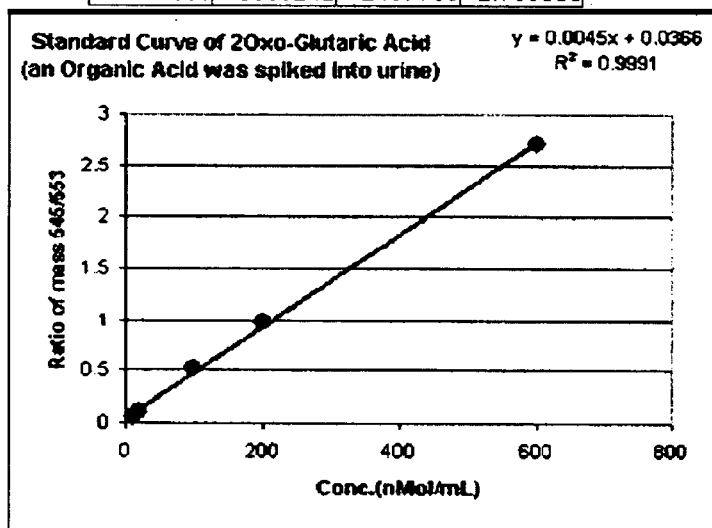
FIG. 11 depicts a standard curve useful for quantitating 2-oxo-glutaric acid in human urine. Standards were prepared from human urine spiked with increasing concentrations of unlabeled 2-oxo-glutaric acid and a constant amount of oxygen-18 labeled 2-oxo-glutaric acid. Standards were extracted, N-methyl-N-(tert-butylmethylsily)-trifluoroacetamide (MTBSTFA) derivatized and analyzed by mass spectrometry. Area under the curve values for labeled and unlabeled organic acid were taken from a GC/positive-EI mass spectrum tracing and used as the input data for the curve.
Figure 12:
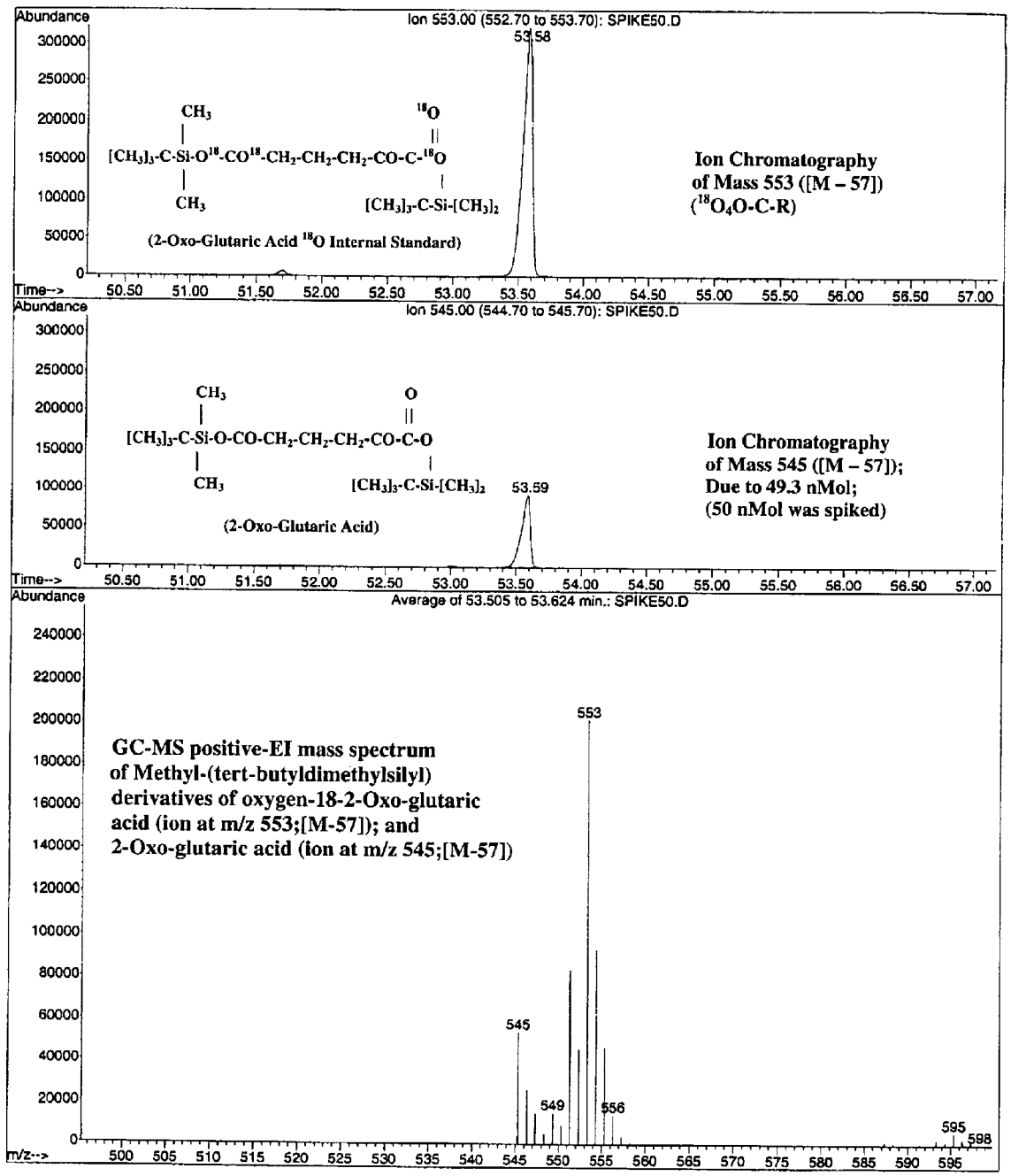
FIG. 12 shows the GC/positive-EI mass spectrum referred to in FIG. 11.

2-Oxo glutaric acid was used as a representative of Oxo-acids (keto-acids). FIG. 11 shows a calibration curve for 2-Oxo glutaric acid, based on the signal peak areas of ion chromatography at m/z 545 (corresponding to 2-Oxo glutaric acid) and m/z 553 (corresponding to oxygen-18 labeled 2-Oxo glutaric acid), with a linearity over a range of 10 to 600 nMol/mL in human urine and a high reliability ($r^2$=0.9991). Measured concentrations of the pooled quality controls were at levels of 22 and 511 nMol/mL, compared with known QC concentrations at 25 and 500 nMol/mL, and showed satisfactory accuracy of the quantitative range. Errors between spiked concentrations of 2-Oxo glutaric acid (at levels of 50 and 200 nMol/mL, respectively) and measured concentrations of 2-Oxo glutaric acid (at levels of 49 and 208 nMol/mL, respectively) were less than 20% (FIG. 11). FIG. 12 shows a representative GC-MS ion chromatography of 2-Oxo glutaric acid and its oxygen 18 labeled internal standard used in the assay.

Example 9

Use of Oxygen-18 Labeled Organic Acids as Internal Standards in Quantitatively Analyzing a Mixture of Organic Acids in Human Urine Samples A method for quantitatively analyzing a mixture of organic acids in human urine (spiked known amounts of organic acids to normal human urine as 'biological samples") using Oxygen-18 labeled organic acids as internal standards is described below. The experimental procedure including liquid/liquid extraction of organic acids from biological samples, chemical derivatization of purified organic acids, and GC-MS analysis of derivatized organic acids was performed as described in Example 7 with additional details below.

Experimental Design for Quantitatively Analyzing a Mixture of Organic Acids:

Step-1: the preparation of calibration standard solutions, pooled quality controls and "biological samples" (spiked known amounts of an organic acid into normal human urine); Calibration standard solutions, a mixture of organic acids, were prepared in human urine at concentrations of 10, 20, 100, 200 and 600 nMol/mL. Pooled quality controls were prepared in human urine at concentrations of 25, 150 and 500 nMol/mL. Finally, 50 and 400 nMol/mL of a mixture of organic acids were spiked into human urine as "biological samples" in order to evaluate accuracy of the methodology.
Step-2: sample extraction, chemical derivatization and GC-MS analysis (as shown in Example 7)
Step-3: the preparation of calibration curves for quantitatively analyzing organic acids in human urine samples;
Step-4: Calculation of the result and data evaluation.

Figure 13:
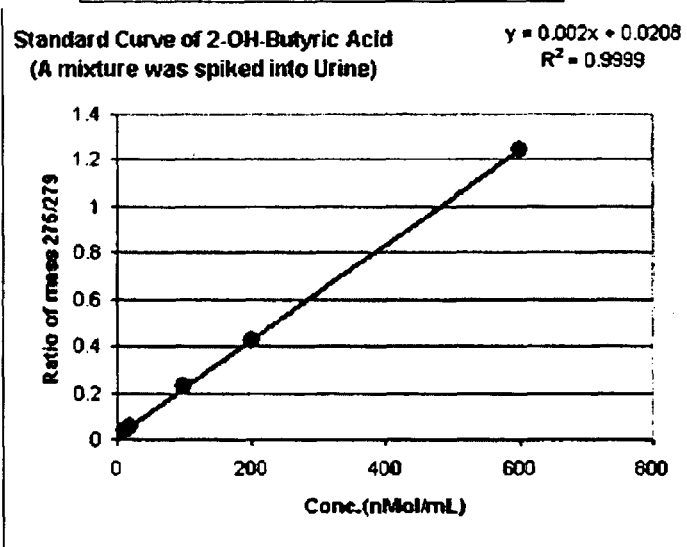
FIG. 13 depicts a standard curve useful for quantitating 2-oxo-glutaric acid in human urine. Standards were prepared from human urine spiked with increasing concentrations of unlabeled 2-OH-butyric acid and a constant amount of oxygen-18 labeled 2-OH-butyric acid. Standards were extracted, MTBSTFA derivatized and analyzed by mass spectrometry. Area under the curve values for labeled and unlabeled organic acid were taken from a GC/positive-EI mass spectrum tracing and used as the input data for the curve.
Figure 14:
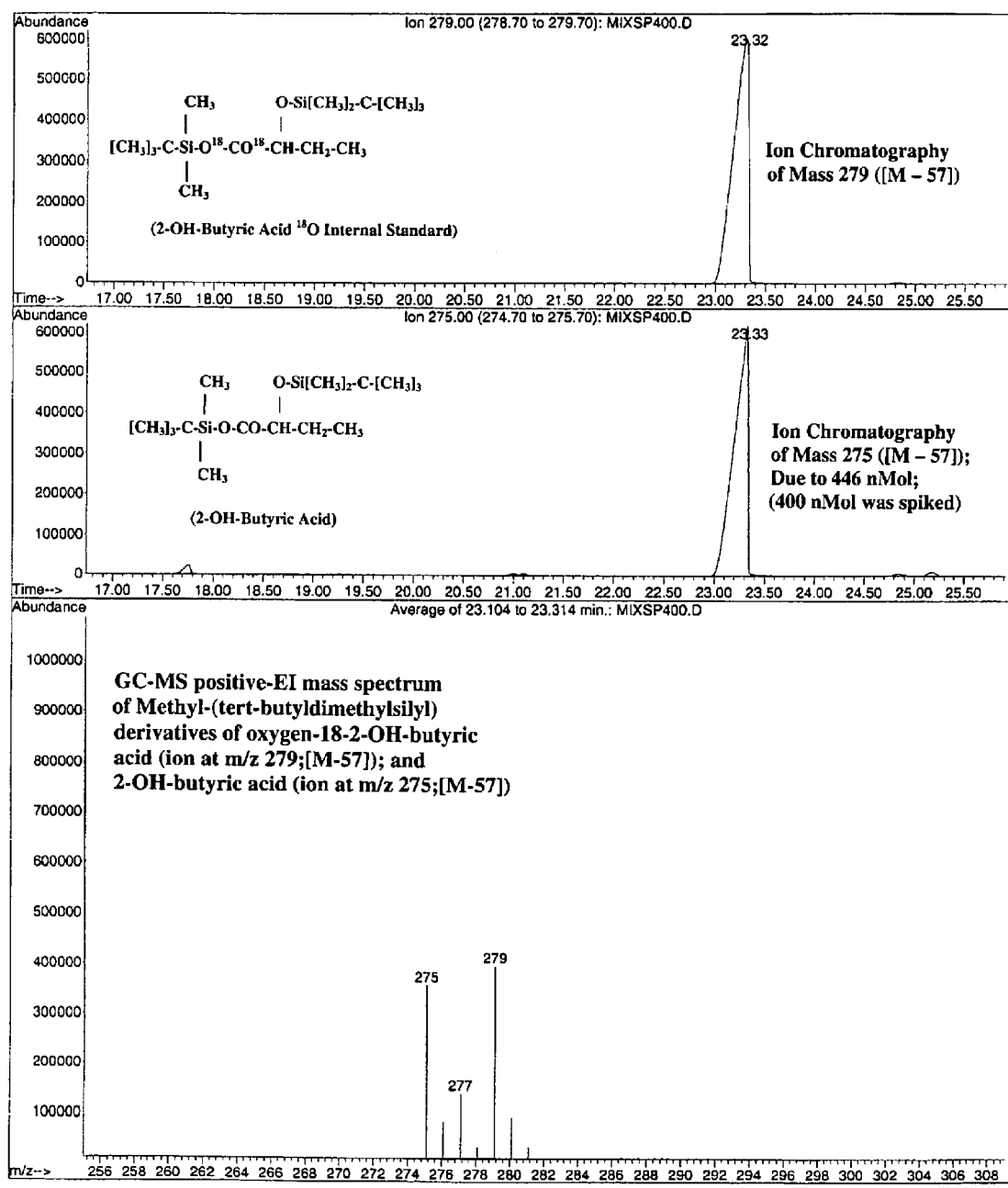
FIG. 14 shows the GC/positive-EI mass spectrum referred to in FIG. 13.

2-OH-butyric acid was used as a representative of 3- and 4-carbon-containing hydroxyl mono acids and was quantitatively analyzed in a mixture of organic acids using oxygen-18 labeled 2-OH-butyric acid as internal standard. FIG. 13 shows a calibration curve for 2-OH-butyric acid, based on the signal peak areas of ion chromatography at m/z 275 (corresponding to 2-OH butyric acid) and m/z 279 (corresponding to oxygen-18 labeled 2-OH butyric acid), with a linearity over a range of 10 to 600 nMol/mL in human urine and a high reliability ($r^2$=0.9999). Measured concentrations of the pooled quality controls were at levels of 28, 155 and 464 nMol/mL, compared with known levels at 25, 150 and 500 nMol/mL, and showed satisfactory accuracy of the quantitative range. Errors between spiked concentrations of 2-OH butyric acid (at levels of 50 and 400 nMol/mL, respectively) and measured concentrations of 2-OH butyric acid (at levels of 52 and 446 nMol/mL, respectively) were less than 20% (FIG. 13). FIG. 14 shows a representative GC-MS ion chromatography and mass spectrum of methyl-(tert-butyldimethylsilyl)-derivative of 2-OH butyric acid and its oxygen 18 labeled internal standard used in the assay.

Figure 15:
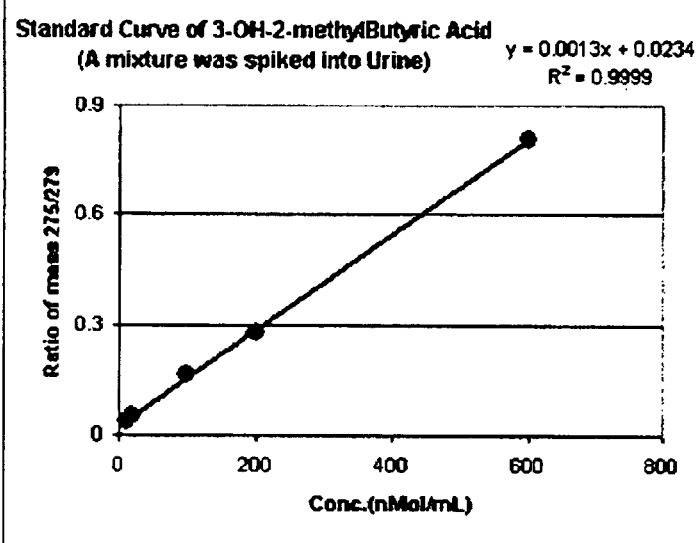
FIG. 15 depicts a standard curve useful for quantitating 2-oxo-glutaric acid in human urine. Standards were prepared from human urine spiked with increasing concentrations of unlabeled 3-OH-3-methyl butyric acid and a constant amount of oxygen-18 labeled 3-OH-3-methyl butyric acid. Standards were extracted, MTBSTFA derivatized and analyzed by mass spectrometry. Area under the curve values for labeled and unlabeled organic acid were taken from a GC/positive-EI mass spectrum tracing and used as the input data for the curve.
Figure 16:
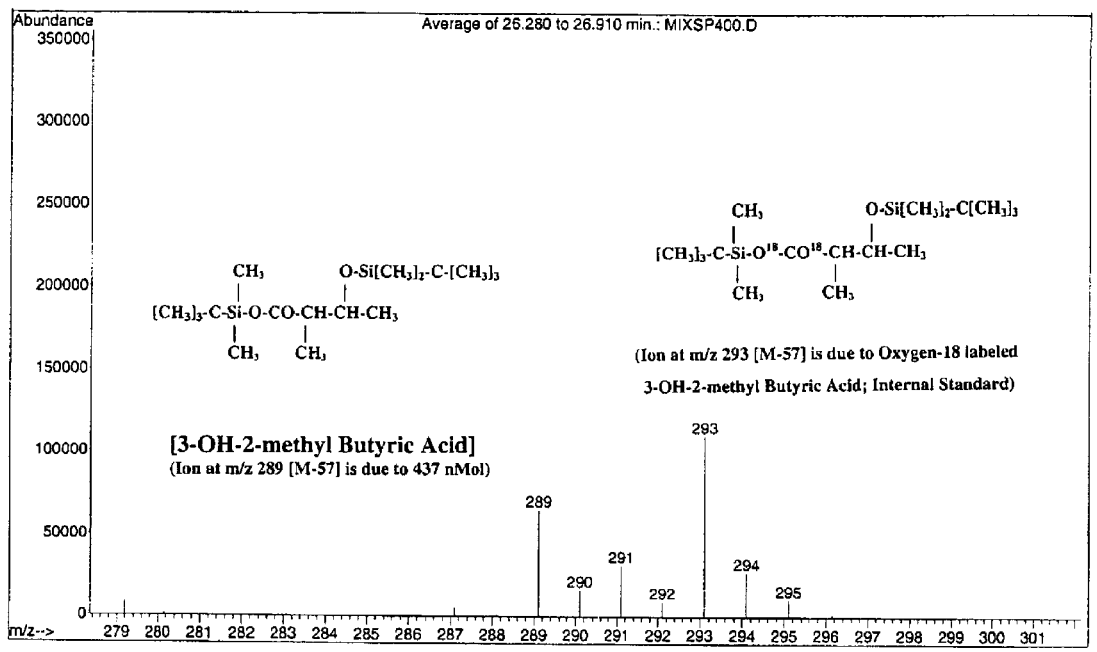
FIG. 16 shows the GC/positive-EI mass spectrum referred to in FIG. 15.

3-OH-2-methyl butyric acid was used as a representative of 5 carbon-containing hydroxyl mono acids and was quantitatively analyzed in a mixture of organic acids using oxygen-18 labeled 3-OH-2-methyl butyric acid as internal standard. FIG. 15 shows a calibration curve for 3-OH-2-methyl butyric acid, based on the intensities of ions at m/z 289 (corresponding to 3-OH-2-methyl butyric acid) and m/z 293 (corresponding to oxygen-18 labeled 2-OH butyric acid), with a linearity over a range of 10 to 600 nMol/mL in human urine and a high reliability ($r^2$=0.9999). Measured concentrations of the pooled quality controls were at levels of 30, 154 and 439 nMol/mL, compared with known QC levels at levels of 25, 150 and 500 nMol/mL, and showed satisfactory accuracy of the assay range. Errors between spiked concentrations of 3-OH-2-methyl butyric acid (at levels of 50 and 400 nMol/mL, respectively) and measured concentrations of 3-OH-2-methyl butyric acid (at levels of 52 and 437 nMol/mL, respectively) were less than 20% (FIG. 15). FIG. 16 shows a representative GC-MS mass spectrum of methyl-(tert-butyldimethylsilyl)-derivative of 3-OH-2-methyl butyric acid and its oxygen 18 labeled internal standard used in the assay.

Figure 17:
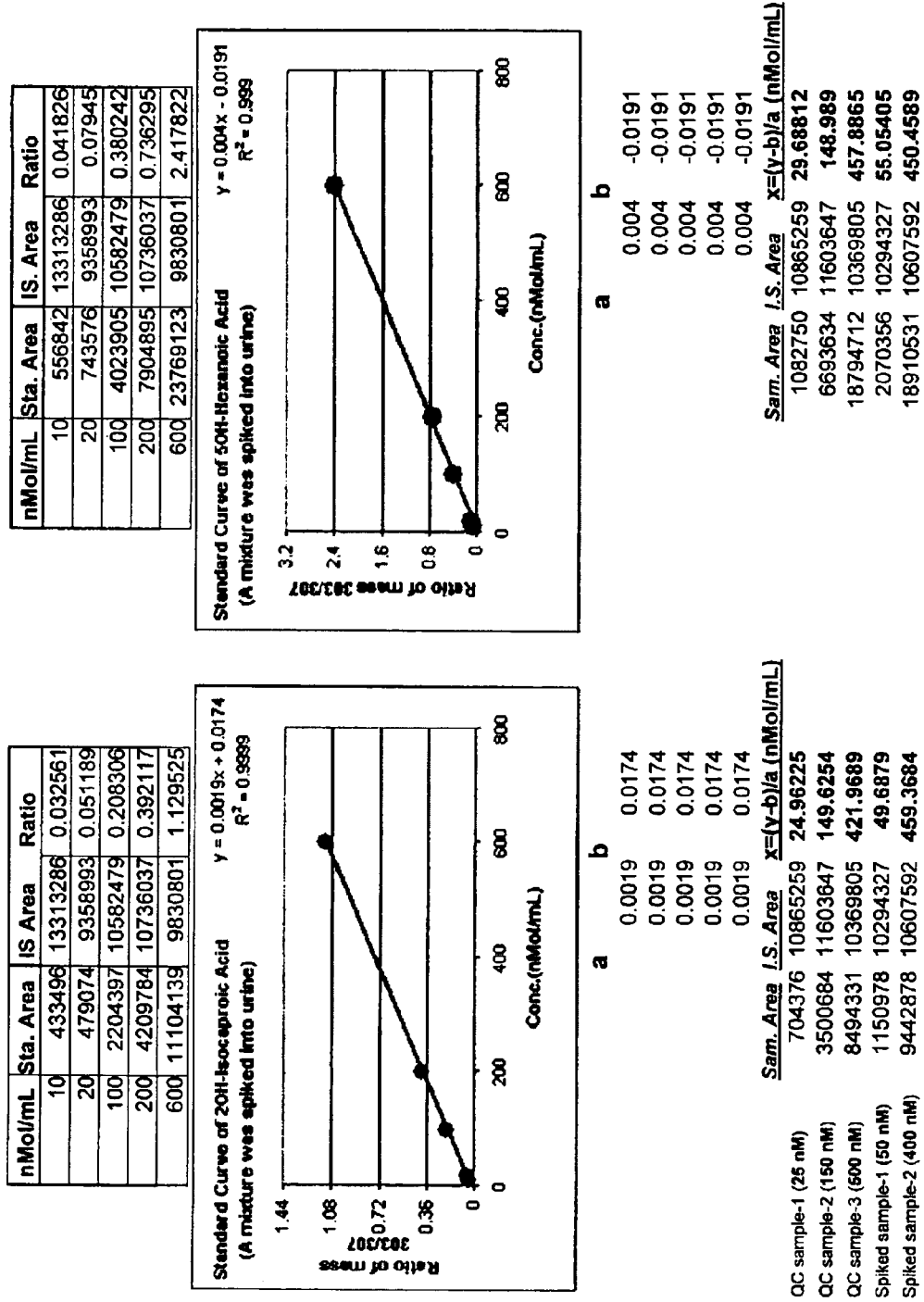
FIG. 17 depicts a standard curve useful for quantitating either 2-OH-isocaproic acid (left side) or 5-OH-hexanoic acid (right side) in human urine. Standards were prepared from human urine spiked with increasing concentrations of either unlabeled 2-OH-isocaproic acid or 5-OH-hexanoic acid and a constant amount of oxygen-18 labeled 2-OH-isocaproic acid. Standards were extracted, MTBSTFA derivatized and analyzed by mass spectrometry. Area under the curve values for labeled and unlabeled organic acid were taken from a GC/positive-EI mass spectrum tracing of unlabeled and labeled 2-OH-isocaproic acid or labeled 2-OHisocaproic acid and unlabeled 5-OH-hexanoic. The curves were generated with data from the tracings.
Figure 18:
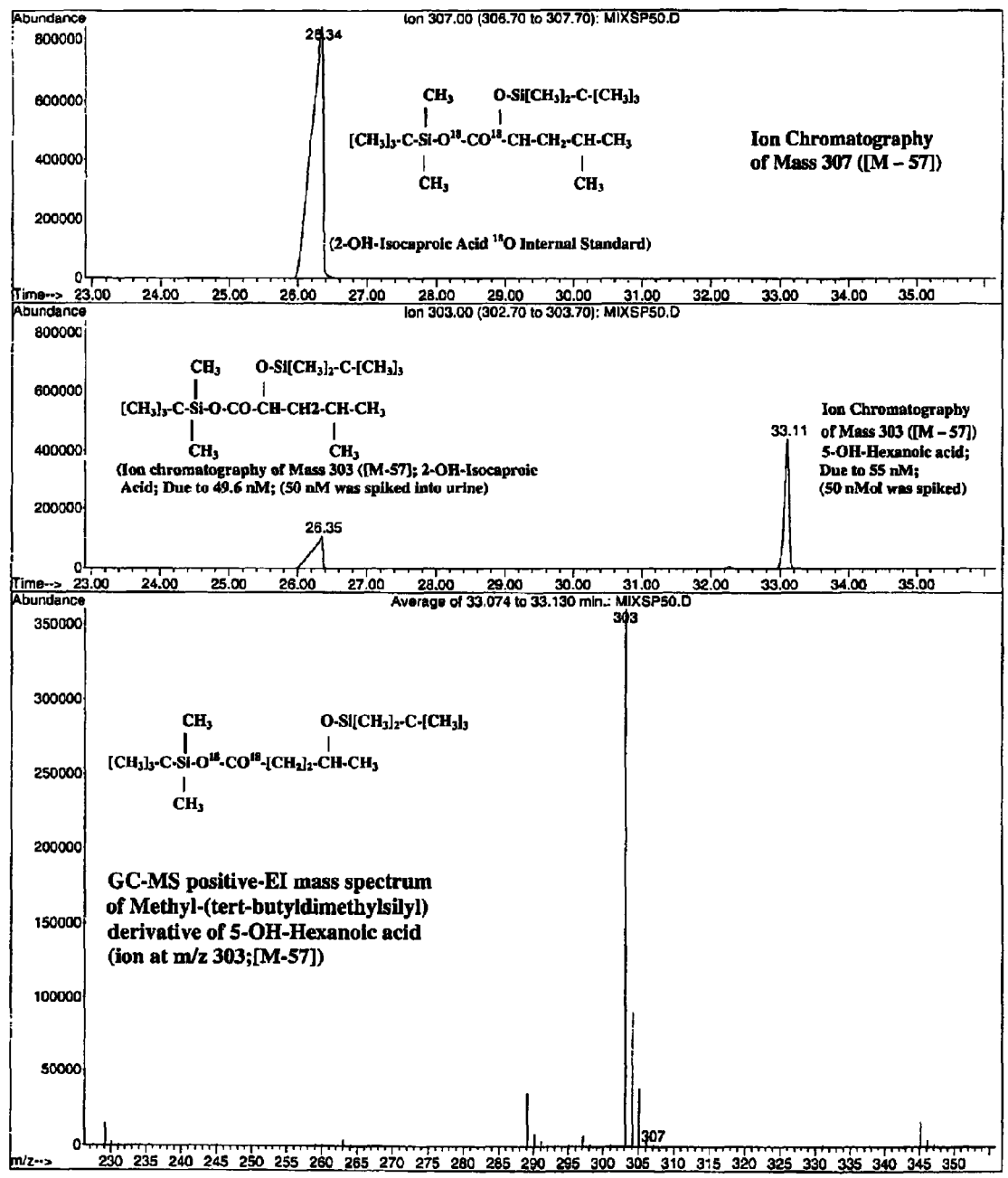
FIG. 18 shows the GC/positive-EI mass spectrums referred to in FIG. 17.

2-OH-isocaproic acid and 5-OH-hexanoic acid were used as representatives of 5 carbon-containing hydroxyl monoacids and were quantitatively analyzed in a mixture of organic acids using oxygen-18 labeled 2-OH-butyric acid as internal standard (a compound for quantitative analyzing structurally identical and similar organic acids). FIG. 17 shows calibration curves for 2-OH-isocaproic and 5-OH-hexanoic acids, based on the signal peak areas of ion chromatography at m/z 303 (corresponding to both 2-OH-isocaproic and 5-OH-hexanoic acids, respectively) and m/z 307 (corresponding to oxygen-18 labeled 2-OH-caproic acid), with a linearity over a range of 10 to 600 nMol/mL in human urine and a high reliability ($r^2$=0.9999 for 2-OH-Isocaproic acid; and $r^2$=0.999 for 5-OH-Hexanoic acid, respectively). Although the two compounds are isomers, they can be readily separated by GC column in different retention times at 26 and 33 minutes, respectively. Measured concentrations of the pooled quality controls are at levels of 25, 150 and 421 nMol/mL (2-OH-caproic acid), as well as at levels of 30, 149 and 458 nMol/mL(5-OH-hexanoic acid), compared with known QC levels at 25, 150 and 500 nMol/mL, and showed satisfactory accuracy of the assay range. Errors between spiked concentrations of the two organic acids (50 and 400 nMol/mL, respectively) and measured concentrations of 2-OH-caproic (at levels of 50 and 459 nMol/mL) as well as 5-OH-hexanoic acids (at levels of 55 and 450 nMol/mL, respectively) were less than 20% (FIG. 17). FIG. 18 shows a representative GC-MS ion chromatography and mass spectrum of methyl-(tert-butyldimethylsilyl)-derivative of 2-OH-caproic and 5-OH-hexanoic acids and oxygen 18 labeled internal standard used in the assay.

Figure 19:
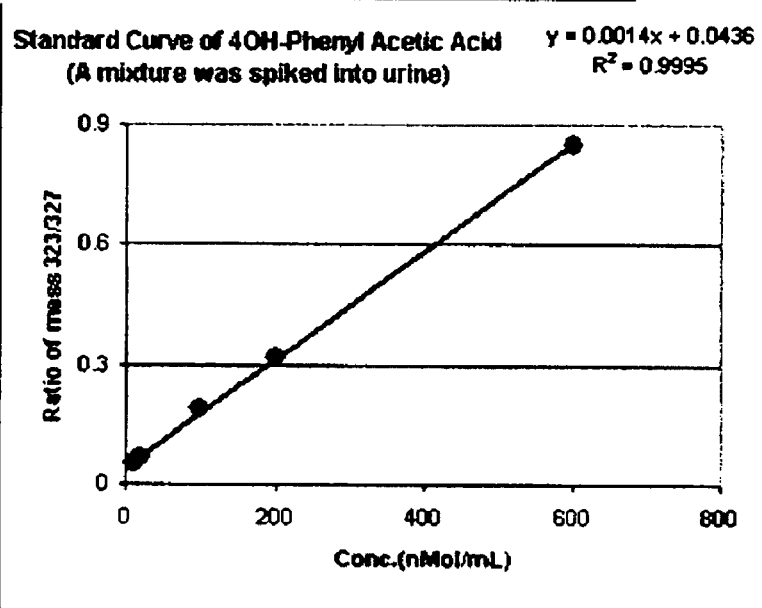
FIG. 19 depicts a standard curve useful for quantitating 4-OH-phenyl acetic acid in human urine. Standards were prepared from human urine spiked with increasing concentrations of unlabeled 4-OH-phenyl acetic acid and a constant amount of oxygen-18 labeled 4-OH-phenyl acetic acid. Standards were extracted, MTBSTFA derivatized and analyzed by mass spectrometry. Area under the curve values for labeled and unlabeled organic acid were taken from a GC/positive-EI mass spectrum tracing and used as the input data for the curve.
Figure 20:
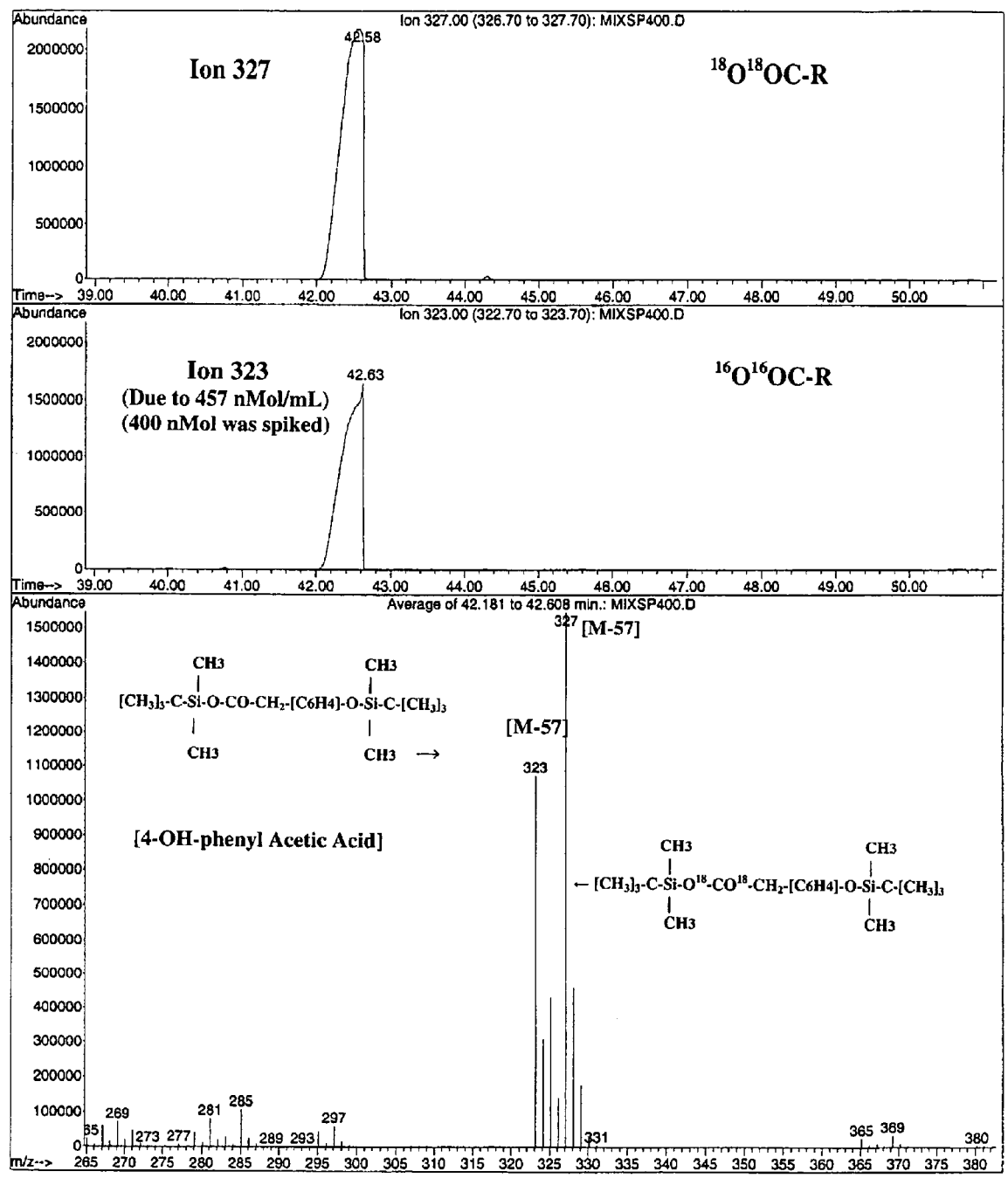
FIG. 20 shows the GC/positive-EI mass spectrum referred to in FIG. 19.

4-OH-phenyl acetic acid was used as a representative of 8-carbon-containing hydroxyl mono acids and was quantitatively analyzed in a mixture of organic acids using oxygen-18 labeled 4-OH-phenyl acetic acid as internal standard. FIG. 18 shows a calibration curve for 4-OH-phenyl acetic acid, based on the signal peak areas of ion chromatography at m/z 323 (corresponding to 4-OH phenyl acetic acid) and m/z 327 (corresponding to oxygen-18 labeled 4-OH phenyl acetic acid), with a linearity over a range of 10 to 600 nMol/mL in human urine and a high reliability ($r^2$=0.9995). Measured concentrations of the pooled quality controls were at levels of 22, 141 and 414 nMol/mL, compared with known QC levels at 25, 150 and 500 nMol/mL, and showed satisfactory accuracy of the quantitative range. Errors between and spiked concentrations of 4-OH phenyl acetic acid (at levels of 50 and 400 nMol/mL, respectively) and measured concentrations of 4-OH phenyl acetic acid (at levels of 48 and 457 nMol/mL, respectively) were less than 20% (FIG. 19). FIG. 20 shows a representative GC-MS ion chromatography and mass spectrum of methyl-(tert-butyldimethylsilyl)-derivative of 4-OH phenyl acetic acid and its oxygen 18 labeled internal standard used in the assay.

Figure 21:
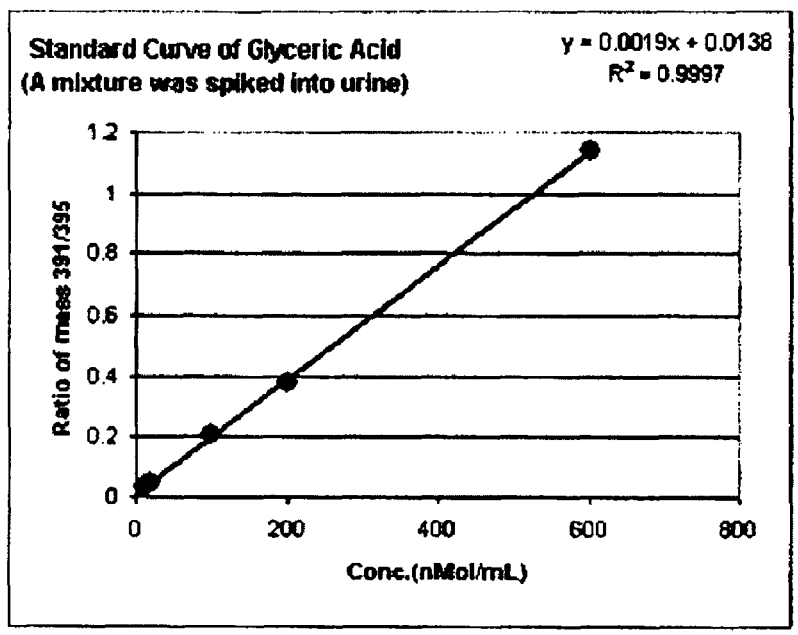
FIG. 21 depicts a standard curve useful for quantitating glyceric acid in human urine. Standards were prepared from human urine spiked with increasing concentrations of unlabeled glyceric acid and a constant amount of oxygen-18 labeled glyceric acid. Standards were extracted, MTBSTFA derivatized and analyzed by mass spectrometry. Area under the curve values for labeled and unlabeled organic acid were taken from a GC/positive-EI mass spectrum tracing and used as the input data for the curve.
Figure 22:
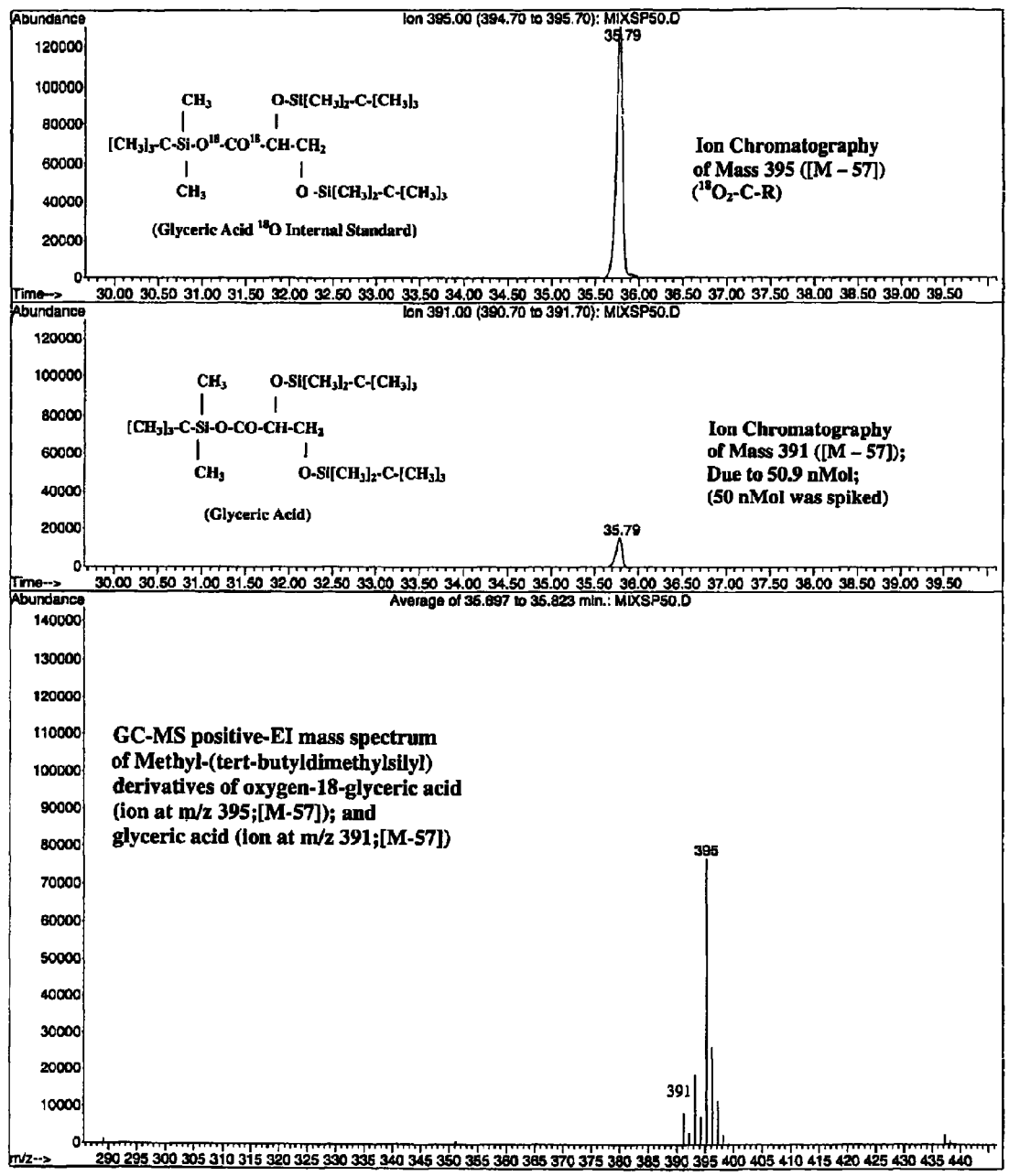
FIG. 22 shows the GC/positive-EI mass spectrum referred to in FIG. 21.

Glyceric acid is a representative of di-hydroxyl mono acids and was quantitatively analyzed in a mixture of organic acids using oxygen-18 labeled glyceric acid as internal standard. FIG. 21 shows a calibration curve for glyceric acid, based on the signal peak areas of ion chromatography at m/z 391 (corresponding to glyceric acid) and m/z 395 (corresponding to oxygen-18 labeled glyceric acid), with a linearity over a range of 10 to 600 nMol/mL in human urine and a high reliability ($r^2$=0.9997). Measured concentrations of the pooled quality controls are at levels of 31, 152 and 472 nMol/mL, compared with known QC levels at 25, 150 and 500 nMol/mL, and showed satisfactory accuracy of the assay range. Errors between spiked concentrations of glyceric acid (at levels of 50 and 400 nMol/mL, respectively) and measured concentrations of glyceric acid (at levels of 51 and 427 nMol/mL, respectively) were less than 20% (FIG. 21). FIG. 22 shows a representative GC-MS ion chromatography and mass spectrum of methyl-(tert-butyldimethylsilyl)-derivative of glyceric acid and its oxygen 18 labeled internal standard used in the assay.

Figure 23:
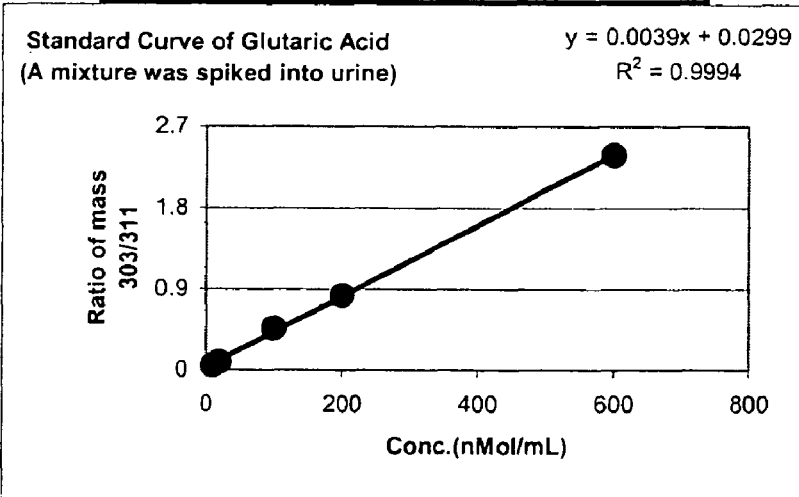
FIG. 23 depicts a standard curve useful for quantitating glutaric acid in human urine. Standards were prepared from human urine spiked with increasing concentrations of unlabeled glutaric acid and a constant amount of oxygen-18 labeled glutaric acid. Standards were extracted, MTBSTFA derivatized and analyzed by mass spectrometry. Area under the curve values for labeled and unlabeled organic acid were taken from a GC/positive-EI mass spectrum tracing and used as the input data for the curve.
Figure 24:
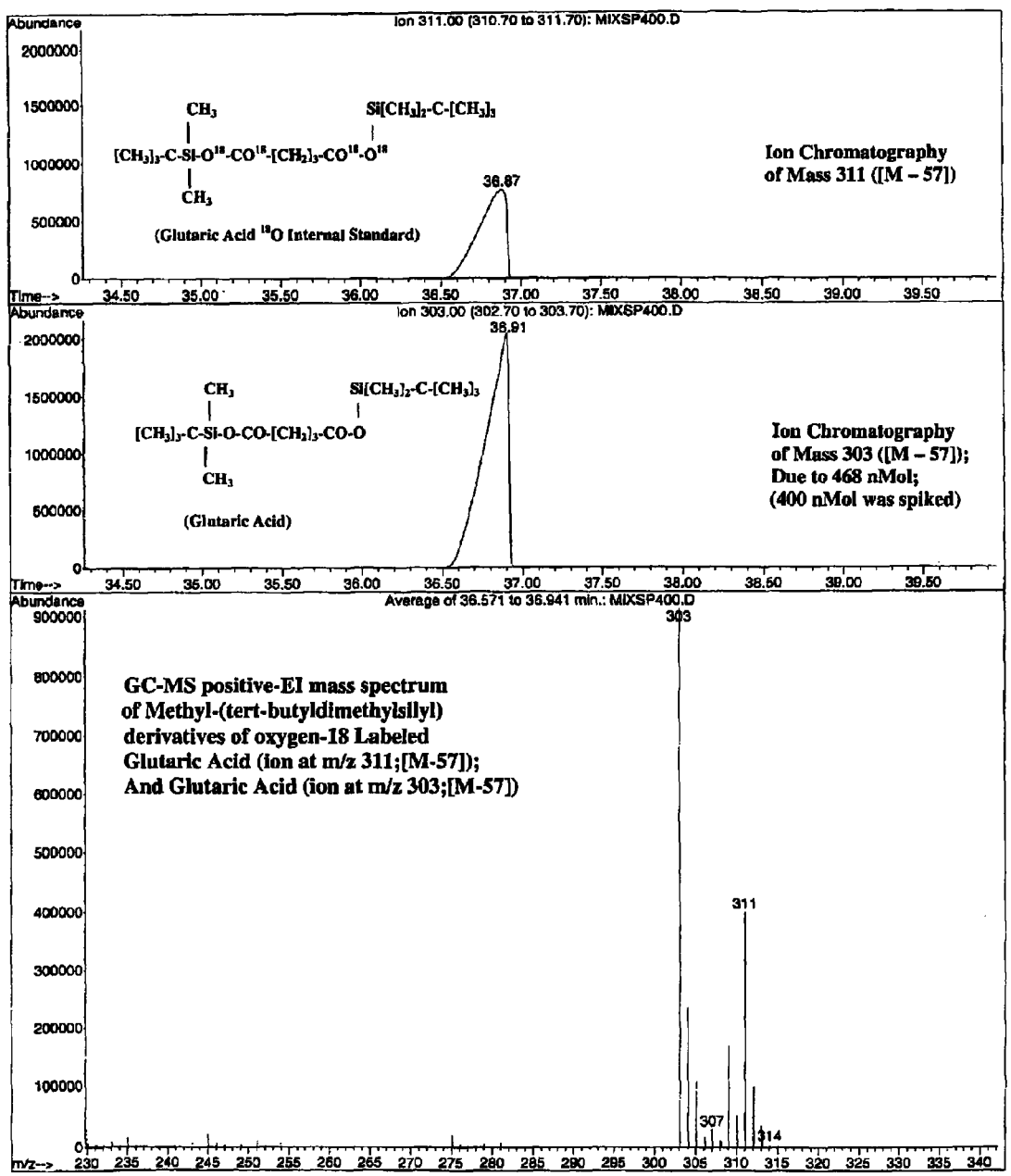
FIG. 24 shows the GC/positive-EI mass spectrum referred to in FIG. 23.

Glutaric acid is a representative of di-acids and was quantitatively analyzed in a mixture of organic acids using oxygen-18 labeled glutaric acid as internal standard. FIG. 23 shows calibration curve for gluteric acid, based on the signal peak areas of ion chromatography of mass 303 (corresponding to gluteric acid) and mass 311 (corresponding to oxygen-18 labeled gluteric acid), with a linearity over a range of 10 to 600 nMol/mL in human urine and a high reliability ($r^2$=0.9994). Measured concentrations of the pooled quality controls were at levels of 25, 158 and 576 nMol/mL, compared with known QC levels at 25, 150 and 500 nMol/mL, and showed satisfactory accuracy of the assay range. Errors between spiked concentrations of gluteric acid (at levels of 50 and 400 nMol/mL, respectively) and measured concentrations of gluteric acid (at levels of 51 and 468 nMol/mL, respectively) were less than 20% (FIG. 23). FIG. 24 shows a representative GC-MS ion chromatography and mass spectrum of methyl-(tert-butyldimethylsilyl)-derivative of gluteric acid and its oxygen 18 labeled internal standard used in the assay.

Figure 25:
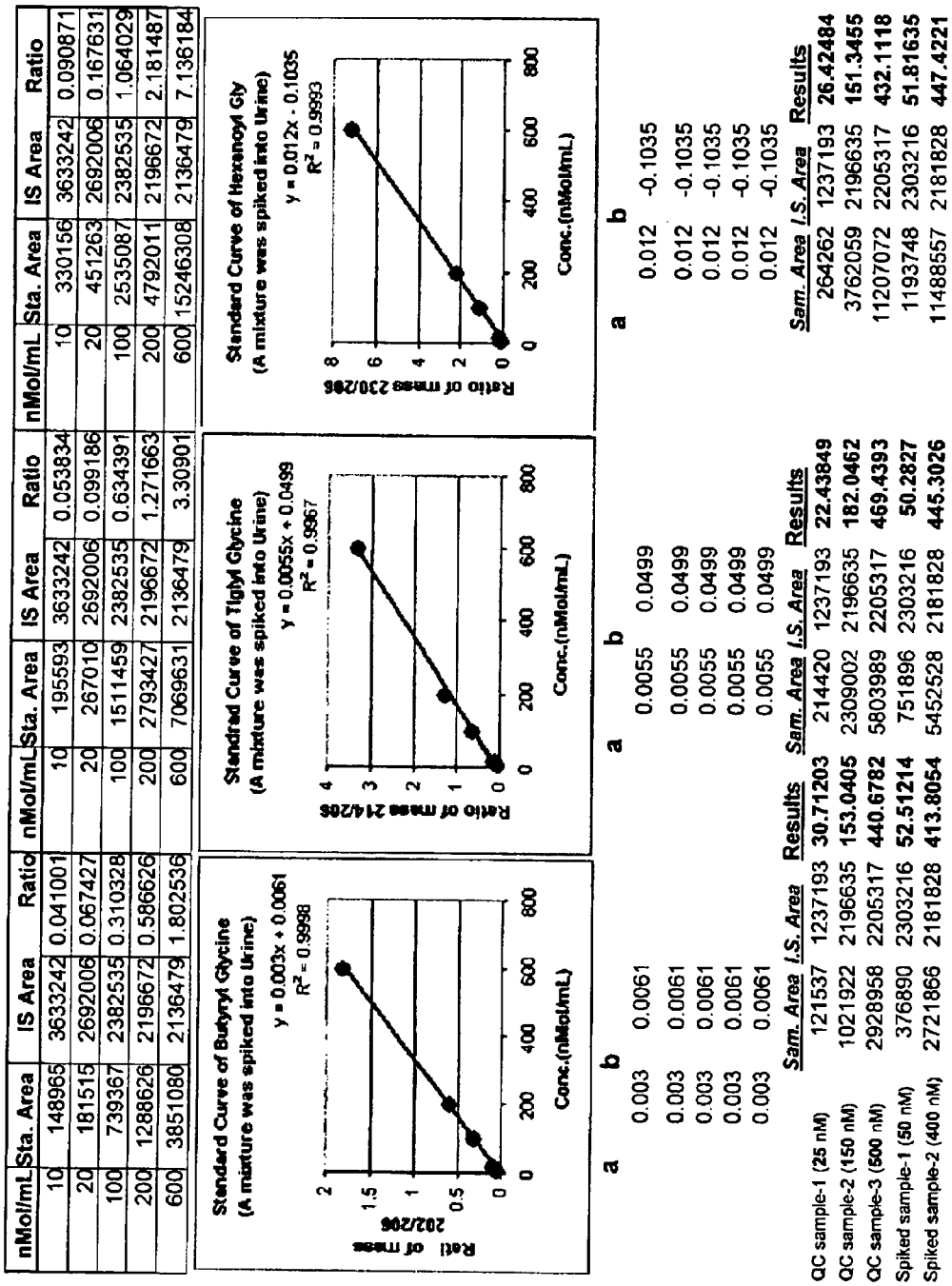
FIG. 25 depicts a standard curve useful for quantitating either butyryl glycine (left side) or tlglyl glycine (middle) or hexanoyl glycine (right side) in human urine. Standards were prepared from human urine spiked with increasing concentrations of either unlabeled butyryl glycine, tlglyl glycine, or hexanoyl glycine and a constant amount of oxygen-18 labeled butyryl glycine. Standards were extracted, MTBSTFA derivatized and analyzed by mass spectrometry. Area under the curve values for labeled and unlabeled organic acid were taken from a GC/positive-EI mass spectrum tracing of unlabeled and labeled butyryl glycine, labeled butyryl glycine and unlabeled tlglyl glycine, and labeled butyryl glycine and unlabeled hexanol glycine. The curves were generated with data from the tracings.
Figure 26:
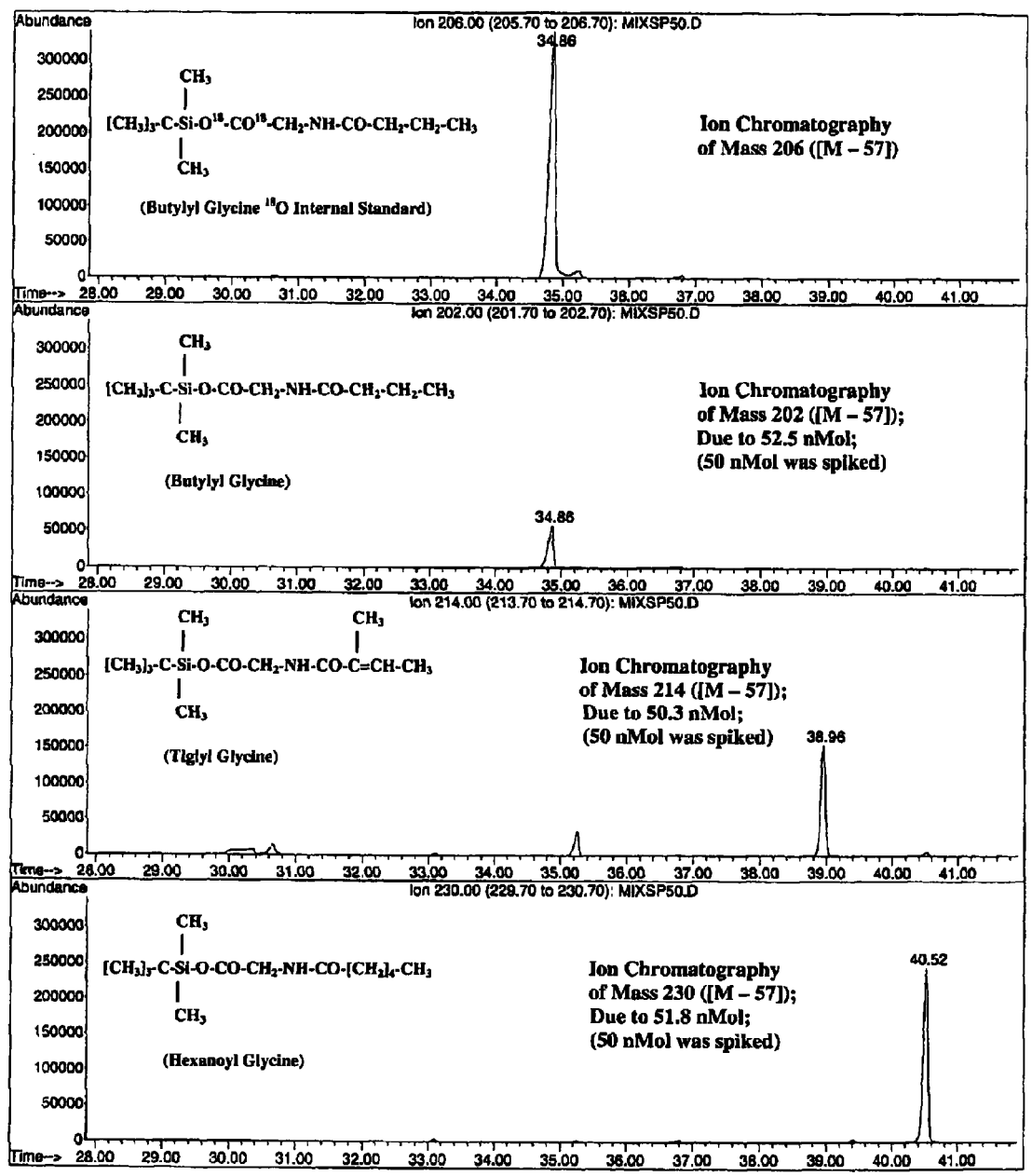
FIG. 26 shows the GC/positive-EI mass spectrums referred to in FIG. 25.

Butyryl, Tlglyl and Hexanoyl glycines were used as representatives of glycine conjugates and were quantitatively analyzed in a mixture of organic acids using oxygen-18 labeled butyryl glycine as internal standard (an internal standard for quantitatively analyzing structurally identical and similar organic acids). FIG. 25 shows calibration curves for butyryl, tlglyl and hexanoyl glycines, based on the signal peak areas of ion chromatography at m/z 202, 214 and 230 (corresponding to Butyryl, Tlglyl and Hexanoyl glycines, respectively) and m/z 206 (corresponding to oxygen-18 labeled Butyryl glycine), with a linearity over a range of 10 to 600 nMol/mL in human urine and a high reliability ($r^2$=0.9998 for Butyryl glycine; $r^2$=0.9967 for Tlglyl glycine; and $r^2$=0.9993 for Hexanoyl glycine, respectively). Measured concentrations of the pooled quality controls were at levels of 31, 153 and 441 nMol/mL for Butyryl glycine; at levels of 22, 182 and 469 nMol/mL for Tlglyl glycine; and at levels of 26, 151 and 432 nMol/mL for Hexanoyl glycine, respectively, compared with known QC levels at 25, 150 and 500 nMol/mL, and showed satisfactory accuracy of the quantitative range. Errors between spiked concentrations of the three organic acids (50 and 400 nMol/mL, respectively) and measured concentrations of Butyryl glycine (53 and 414 nMol/mL), Tlglyl glycine (50 and 445 nMol/mL), and Hexanoyl glycine (52 and 447 nMol/mL) were less than 20% (FIG. 25). FIG. 26 shows a representative GC-MS ion chromatography of methyl-(tert-butyldimethylsilyl)-derivatives of Butyryl, Tlglyl and Hexanoyl glycines, as well as oxygen 18 labeled Butyryl glycine internal standard used in the assay.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other physical and electronic documents. The inventions illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention. The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of measuring the amount of an unlabeled organic acid in a biological sample, comprising:
   a) adding to a biological sample suspected of containing the unlabeled organic acid to be measured an amount of a standard comprising one or more oxygen-18 labeled organic acids, wherein at least one of the oxygen-18 labeled organic acids belongs to an organic acid class selected from the group consisting of dihydroxy monoacid, dicarboxyl organic acid, hydroxyl dicarboxyl acid, tricarboxyl acid, glycine conjugate, glyoxylic acid, hydroxyl mono-acid selected from the group consisting of glycolic acid, lactic acid, 3-hydroxypropionic acid, 2-hydroxybutyric acid, 3-hydroxyisobutyric acid, 3-hydroxybutyric acid, 4-hydroxybutyric acid, 2-hydroxyisovaleric acid, 3-hydroxy-2-methylbutyric acid, 3-hydroxy isovaleric acid, 3-hydroxy-2-ethylpropionic acid, 3-hydroxyvaleric acid, 4-hydroxyisovaleric acid, 5-hydroxyhexanoic acid, 2-hydroxyisocaproic acid, 2-hydroxy-3-methylvaleric acid, 5-hydroxyhexanoic acid, 3-hydroxy-2-methylvaleric acid, 2-hydroxyphenylacetic acid, 4-hydroxy phenylacetic acid, 4-hydroxycyclohexylacetic acid, phenyllacetic acid, 4-hydroxyphenylpropionic acid, 5-hydroxyindoleacetic acid, indoleacetic acid and 3-hydroxydodecanoic acid, and keto acid, and wherein at least one of said oxygen-18 labeled organic acids is structurally similar or identical to the unlabeled organic acid to be measured;
   b) processing the sample to increase the concentration of and/or chemically modify the unlabeled organic acid to be measured;
   c) measuring the amount of unlabeled organic acid and oxygen-18 organic acid in the processed sample by mass spectrometry; and
   d) using the amount of oxygen-18 organic acid measured in step c) to adjust the measured amount of unlabeled organic acid measured in the processed sample so as to reflect the amount of unlabeled organic acid originally present in the sample.

2. The method of claim 1, wherein said mass spectrometry is gas chromatography-mass spectrometry.

3. The method of claim 1, wherein said mass spectrometry is liquid chromatography-mass spectrometry.

4. The method of claim 1, wherein said sample is a urine sample.

5. The method of claim 1 wherein said processing comprises increasing the concentration of the unlabeled organic acid in the sample.

6. The method of claim 1, wherein said processing comprises chemically modifying the unlabeled organic acid in the sample.

7. A method of measuring the amount of at least one unlabeled organic acid in a biological sample, comprising;
   a) adding to a biological sample suspected of containing the at least one unlabeled organic acid to be measured an amount of oxygen-18 labeled organic acids, wherein the oxygen-18 labeled organic acids comprise at least one acid selected from each of hydroxy mono-acid, dihydroxy mono-acid, dicarboxyl organic acid, hydroxyl dicarboxyl acid, tricarboxyl acid, glycine conjugate and keto acid;
   b) processing the sample to increase the concentration of and/or chemically modify the unlabeled organic acid to be measured;
   c) measuring the amount of unlabeled organic acids and oxygen-18 organic acids in the processed sample by mass spectrometry; and
   d) using the amount of an oxygen-18 organic acid measured in step c) to adjust the measured amount of a structurally similar or identical unlabeled organic acid in the processed sample so as to reflect the amount of unlabeled organic acid originally present in the sample.

8. The method of claim 7 wherein at least two oxygen-18 labeled organic acids from each of hydroxy mono-acid, dihydroxy mono-acid, dicarboxyl organic acid, hydroxyl dicarboxyl acid, tricarboxyl acid, glycine conjugate and keto acid are added to said sample.

9. The method of claim 7 wherein at least 3 or more oxygen-18 labeled organic acids from each of hydroxy mono-acid, dihydroxy mono-acid, dicarboxyl organic acid, hydroxyl dicarboxyl acid, tricarboxyl acid, glycine conjugate and keto acid are added to said sample.

10. The method of claim 7 wherein said processing comprises increasing the concentration of the unlabeled organic acid in the sample.

11. The method of claim 7 wherein said processing comprises chemically modifying the unlabeled organic acid in the sample.

12. The method of claim 7, wherein said mass spectrometry is gas chromatography-mass spectrometry.

13. The method of claim 7, wherein said mass spectrometry is liquid chromatography-mass spectrometry.

14. The method of claim 7, wherein said sample is a urine sample.

15. A method of diagnosing an individual with a metabolic defect characterized by an abnormal amount of an unlabeled organic acid in a biological sample of the individual, said method comprising:
   a) adding to a biological sample from the individual an amount of a standard comprising one or more oxygen-18 labeled organic acids, wherein at least one of the oxygen-18 labeled organic acids belong to an organic acid class selected from the group consisting of dihydroxy mono-acid, dicarboxyl organic acid, hydroxyl dicarboxyl acid, tricarboxyl acid, glycine conjugate, glyoxylic acid, hydroxyl mono-acid selected from the group consisting of glycolic acid, lactic acid, 3-hydroxypropionic acid, 2-hydroxybutyric acid, 3-hydroxyisobutyric acid, 3-hydroxybutyric acid, 4-hydroxybutyric acid, 2-hydroxyisovaleric acid, 3-hydroxy-2-methylbutyric acid, 3-hydroxy isovaleric acid, 3-hydroxy-2-ethylpropionic acid, 3-hydroxyvaleric acid, 4-hydroxyisovaleric acid, 5-hydroxyhexanoic acid, 2-hydroxyisocaproic acid, 2-hydroxy-3-methylvaleric acid, 5-hydroxyhexanoic acid, 3-hydroxy-2-methylvaleric acid, 2-hydroxyphenylacetic acid, 4-hydroxy phenylacetic acid, 4-hydroxycyclohexylacetic acid, phenyllacetic acid, 4-hydroxyphenylpropionic acid, 5-hydroxyindoleacetic acid, indoleacetic acid and 3-hydroxydodecanoic acid, and keto acid, and wherein at least one oxygen-18 labeled organic acid is structurally similar or identical to the unlabeled organic acid to be measured;
   b) processing the sample to increase the concentration of and/or chemically modify the unlabeled organic acid to be measured;
   c) measuring the amount of unlabeled organic acid and oxygen-18 organic acid in the processed sample by mass spectrometry;
   d) using the amount of oxygen-18 organic acid measured in step c) to adjust the measured amount of unlabeled organic acid in the processed sample so as to reflect the amount of unlabeled organic acid originally present in the sample; and
   e) determining if the amount of the unlabeled organic acid detected in the sample is an abnormal amount, thereby diagnosing the existence a metabolic defect in the individual.

16. The method of claim 15 wherein said processing comprises increasing the concentration of the unlabeled organic acid in the sample.

17. The method of claim 15 wherein said processing comprises chemically modifying the unlabeled organic acid in the sample.

18. The method of claim 15, wherein said mass spectrometry is gas chromatography-mass spectrometry.

19. The method of claim 15, wherein said mass spectrometry is liquid chromatography-mass spectrometry.

20. The method of claim 15 wherein said sample is a urine sample.

21. A method of diagnosing an individual with a metabolic defect characterized by an abnormal amount of at least one unlabeled organic acid in a sample of the individual, said method comprising:
   a) adding to a sample from the individual an amount of oxygen-18 labeled organic acids, wherein the oxygen-18 labeled organic acids comprise at least one acid selected from each of hydroxy mono-acid, dihydroxy mono-acid, dicarboxyl organic acid, hydroxyl dicarboxyl acid, tricarboxyl acid, glycine conjugate, and keto acid;
   b) processing the sample to increase the concentration of and/or chemically modify the unlabeled organic acid to be measured;
   c) measuring the amount of unlabeled organic acids and oxygen-18 organic acids in the processed sample by mass spectrometry;
   d) using the amount of an oxygen-18 organic acid measured in step c) to adjust the measured amount of a structurally similar or identical unlabeled organic acid in the processed sample so as to reflect the amount of the at least one unlabeled organic acid originally present in the sample; and e) determining if the amount of the at least one unlabeled organic acid originally present in the sample is an abnormal amount, thereby diagnosing the existence a metabolic defect in the individual.

22. The method of claim 21 wherein at least two oxygen-18 labeled organic acids from each of hydroxy mono-acid, dihydroxy mono-acid, dicarboxyl organic acid, hydroxyl dicarboxyl acid, tricarboxyl acid, glycine conjugate and keto acid are added to said sample.

23. The method of claim 21 wherein at least 3 or more oxygen-18 labeled organic acids from each of hydroxy mono-acid, dihydroxy mono-acid, dicarboxyl organic acid, hydroxyl dicarboxyl acid, tricarboxyl acid, glycine conjugate and keto acid are added to said sample.

24. The method of claim 21 wherein said processing comprises increasing the concentration of the unlabeled organic acid in the sample.

25. The method of claim 21 wherein said processing comprises chemically modifying the unlabeled organic acid in the sample.

26. The method of claim 21, wherein said mass spectrometry is gas chromatography-mass spectrometry.

27. The method of claim 21, wherein said mass spectrometry is liquid chromatography-mass spectrometry.

28. The method of claim 21 wherein said sample is a urine sample.

29. The method of claim 1, wherein said oxygen-18 labeled organic acid is a dihydroxy mono-acid.

30. The method of claim 1, wherein said oxygen-18 labeled organic acid is a dicarboxyl organic acid.

31. The method of claim 1, wherein said oxygen-18 labeled organic acid is a hydroxyl dicarboxyl acid.

32. The method of claim 1, wherein said oxygen-18 labeled organic acid is a tricarboxyl acid.

33. The method of claim 1, wherein said oxygen-18 labeled organic acid is a glycine conjugate.

34. The method of claim 1, wherein said oxygen-18 labeled organic acid is a glyoxylic acid.

35. The method of claim 1, wherein said oxygen-18 labeled organic acid is a hydroxyl mono-acid selected from the group consisting of glycolic acid, lactic acid, 3-hydroxypropionic acid, 2-hydroxybutyric acid, 3-hydroxyisobutyric acid, 3-hydroxybutric acid, 4-hydroxybutyric acid, 2-hydroxyisovaleric acid, 3-hydroxy-2-methylbutyric acid, 3-hydroxy isovaleric acid, 3-hydroxy-2-ethylpropionic acid, 3-hydroxyvaleric acid, 4-hydroxyisovaleric acid, 5-hydroxyhexanoic acid, 2-hydroxyisocaproic acid, 2-hydroxy-3-methylvaleric acid, 5-hydroxyhexanoic acid, 3-hydroxy-2-methylvaleric acid, 2-hydroxyphenylacetic acid, 4-hydroxy phenylacetic acid, 4-hydroxycyclohexylacetic acid, phenyllacetic acid, 4-hydroxyphenylpropionic acid, 5-hydroxyindoleacetic acid, indoleacetic acid and 3-hydroxydodecanoic acid.

36. The method of claim 1, wherein said oxygen-18 labeled organic acid is a keto acid.

37. The method of claim 1, wherein said standard comprises at least two oxygen-18 labeled organic acids selected from two different organic acid groups.

38. The method of claim 1, wherein said standard comprises at least three oxygen-18 labeled organic acids selected from three different organic acid groups.

39. The method of claim 1, wherein said standard comprises at least four oxygen-18 labeled organic acids selected from four different organic acid groups.

40. The method of claim 1, wherein the sample is acidic.
41. The method of claim 7, wherein the sample is acidic.
42. The method of claim 15, wherein the sample is acidic.
43. The method of claim 21, wherein the sample is acidic.

* * * * *

UNITED STATES PATENT AND TRADEMARK OFFICE
CERTIFICATE OF CORRECTION

| | |
|---|---|
| PATENT NO. | : 7,993,931 B1 |
| APPLICATION NO. | : 10/696051 |
| DATED | : August 9, 2011 |
| INVENTOR(S) | : Su Chen |

It is certified that error appears in the above-identified patent and that said Letters Patent is hereby corrected as shown below:

Column 28, line 55, delete the word "Succinyacetone" and replace with

-- Succinylacetone--.

Column 28, line 59, delete the word "Succinyacetone" and replace with

-- Succinylacetone--.

Column 28, line 61, delete the word "Succinyacetone" and replace with

-- Succinylacetone--.

Column 31, line 51, delete the word "Succinyacetone" and replace with

-- Succinylacetone --.

Column 36, line 65, delete the phrase "acid measured in" and replace with -- acid in. --.

Signed and Sealed this
Twenty-ninth Day of November, 2011

David J. Kappos
*Director of the United States Patent and Trademark Office*